(12) United States Patent
Huopana

(10) Patent No.: US 12,313,429 B2
(45) Date of Patent: May 27, 2025

(54) DEVICE FOR MEASUREMENTS FOR A WEARABLE DEVICE SENSOR

(71) Applicant: Oura Health Oy, Oulu (FI)

(72) Inventor: Jouni Huopana, Oulu (FI)

(73) Assignee: Oura Health Oy, Oulu (FI)

( * ) Notice: Subject to any disclaimer, the term of this patent is extended or adjusted under 35 U.S.C. 154(b) by 0 days.

(21) Appl. No.: 18/738,097

(22) Filed: Jun. 10, 2024

(65) Prior Publication Data

US 2024/0410725 A1    Dec. 12, 2024

Related U.S. Application Data

(60) Provisional application No. 63/507,494, filed on Jun. 12, 2023.

(51) Int. Cl.
*G01D 18/00* (2006.01)
*A61B 5/00* (2006.01)
*G01D 5/26* (2006.01)

(52) U.S. Cl.
CPC .............. *G01D 18/00* (2013.01); *G01D 5/26* (2013.01); *A61B 5/6801* (2013.01)

(58) Field of Classification Search
CPC ....... A61B 5/68; A61B 5/6801; A61B 5/6802; A61B 5/6803; A61B 5/6804; A61B 5/6807; A61B 5/681; A61B 5/6813; A61B 5/6814; A61B 5/6815; A61B 5/6816; A61B 5/6817; A61B 5/6819; A61B 5/682; A61B 5/6821; A61B 5/6822; A61B 5/6823; A61B 5/6824; A61B 5/6825; A61B 5/6826; A61B 5/6828; A61B 5/6829; A61B 5/6844; A61B 5/74; A61B 5/74268; G01D 18/00; G01D 18/001; G01D 18/002; G01D 18/004; G01D 18/006; G01D 18/008; G01D 5/26; G01D 5/264; G01D 5/30; G01D 5/305
See application file for complete search history.

(56) References Cited

U.S. PATENT DOCUMENTS

| | | | |
|---|---|---|---|
| 10,939,835 B2* | 3/2021 | Aliamiri | A61B 5/0245 |
| 11,129,572 B2* | 9/2021 | Just | A61B 5/6816 |
| 11,781,907 B2* | 10/2023 | Capella | G01J 1/0271 |
| | | | 600/310 |
| 2009/0169078 A1* | 7/2009 | Ozawa | A61B 5/1455 |
| | | | 382/128 |
| 2016/0206212 A1* | 7/2016 | Lee | A61B 5/02055 |
| 2017/0119314 A1* | 5/2017 | Just | A61B 5/6844 |
| 2018/0156660 A1* | 6/2018 | Turgeon | G01J 1/44 |
| 2018/0338721 A1* | 11/2018 | Wang | A61B 5/0205 |
| 2019/0142288 A1* | 5/2019 | Aliamiri | A61B 5/6885 |
| | | | 600/301 |
| 2020/0085306 A1* | 3/2020 | To | A61B 5/681 |
| 2022/0015707 A1* | 1/2022 | Just | A61B 5/6843 |

(Continued)

*Primary Examiner* — John R Lee
(74) *Attorney, Agent, or Firm* — Espatent Oy

(57) ABSTRACT

In accordance with an example embodiment, there is provided a device for measurements for a wearable device sensor, the device comprising: a support configured to receive an appendage of a human body; at least one light source; at least one light detector; and an actuator configured to move the at least one light source, or the at least one light detector, or both to at least two different measurement positions in relation to the support.

24 Claims, 11 Drawing Sheets

(56) References Cited

U.S. PATENT DOCUMENTS

| | | | |
|---|---|---|---|
| 2023/0079736 A1* | 3/2023 | Mäkinen | G01N 21/4133 |
| | | | 600/300 |
| 2023/0096307 A1* | 3/2023 | Vallius | G16H 40/67 |
| | | | 600/474 |
| 2023/0190197 A1* | 6/2023 | Huttunen | A61B 5/6826 |
| | | | 600/301 |

* cited by examiner a) b)

a) b)

910. Arranging a light source and a light detector around an appendage of a human body 920. Automatically moving the light source, the light detector, or both to at least two different measurement positions 930. Collecting information relating to light detected by the light detector form the at least two different measurement positions 940. Optionally, providing the collected information for optimizing locations of light sources, locations of light detectors, wavelengths that are used

Fig. 9

DEVICE FOR MEASUREMENTS FOR A WEARABLE DEVICE SENSOR

TECHNICAL FIELD

Various example embodiments relate to wearable devices and a device for measurements for a wearable device sensor.

BACKGROUND

This section illustrates useful background information without admission of any technique described herein representative of the state of the art.

Some wearable devices may be configured to collect data from users, including temperature data, heart rate data, motion data, and the like. However, there may be variability between users that may cause inconsistencies in the data. There are many factors that need to be considered when developing such wearable devices.

SUMMARY

The scope of protection sought for various embodiments of the invention is set out by the independent claims. The embodiments and features, if any, described in this specification that do not fall under the scope of the independent claims are to be interpreted as examples useful for understanding various embodiments of the invention.

According to a first example aspect, there is provided a device for measurements for a wearable device sensor. The device may be used for example for test measurements for the purposes of development of the wearable device sensor. The device comprises
   a support configured to receive an appendage of a human body;
   at least one light source;
   at least one light detector; and
   an actuator configured to move the at least one light source, or the at least one light detector, or both to at least two different measurement positions in relation to the support.

In some embodiments, the actuator is configured to rotate the at least one light source, or the at least one light detector, or both around the support.

In some embodiments, the actuator is configured to automatically move the at least one light source, or the at least one light detector, or both.

In some embodiments, the actuator is configured to move both the at least one light source and the at least one light detector in synchronization.

In some embodiments, the actuator is configured to move the at least one light source and the at least one light detector independently from each other.

In some embodiments, the actuator comprises a motor.

In some embodiments, the actuator comprises a manual pivot.

In some embodiments, the at least one light source and the at least one light detector are positioned substantially on opposite sides of the support.

In some embodiments, the light detector is a spectrometer.

In some embodiments, the light source has a wide wavelength range. The wide wavelength range may extend outside visible light wavelengths. Additionally or alternatively, the wide wavelength range may extend from infrared wavelengths to ultraviolet wavelengths.

In some embodiments, the light source emits white light.

In some embodiments, the device comprises two or more of said light sources.

In some embodiments, the device comprises two or more of said light detectors.

In some embodiments, the device comprises an output configured to output information relating to light detected by the at least one light detector at the at least two different measurement positions.

In some embodiments, the appendage of a human body is a wrist, an ankle, an arm, a leg, a finger, a toe, or an ear lobe.

According to a second example aspect, there is provided a method comprising
   performing measurement for a wearable device sensor by arranging at least one light source and at least one light detector around an appendage of a human body;
   automatically moving the at least one light source, or the at least one light detector, or both to at least two different measurement positions in relation to the appendage of a human body, and
   collecting information relating to light detected by the at least one light detector from the at least two different measurement positions.

In some embodiments, automatically moving the at least one light source, or the at least one light detector, or both comprises rotating the at least one light source, or the at least one light detector, or both around the appendage of the human body.

In some embodiments, automatically moving the at least one light source, or the at least one light detector, or both comprises moving both the at least one light source and the at least one light detector in synchronization.

In some embodiments, automatically moving the at least one light source, or the at least one light detector, or both comprises moving the at least one light source and the at least one light detector independently from each other.

In some embodiments, the method of the second aspect further comprises providing the collected information for optimizing one or more of the following in a wearable device sensor: location of one or more light sources, location of one or more light detectors, wavelengths used in the wearable device sensor.

According to a third example aspect, there is provided a computer program comprising computer executable program instructions configured to cause performing the method of the second example aspect or any related embodiment.

In some embodiments, the computer program may be stored in a computer readable memory medium.

Different non-binding example aspects and embodiments have been illustrated in the foregoing. The embodiments in the foregoing are used merely to explain selected aspects or steps that may be utilized in implementations. Some embodiments may be presented only with reference to certain example aspects of the invention. It should be appreciated that corresponding embodiments may apply to other example aspects as well.

BRIEF DESCRIPTION OF THE DRAWINGS

For a more complete understanding of example embodiments, reference is now made to the following descriptions taken in connection with the accompanying drawings in which:

FIG. 9 shows a flow chart of a method of an example embodiment.

DETAILED DESCRIPTION

Figure 1:
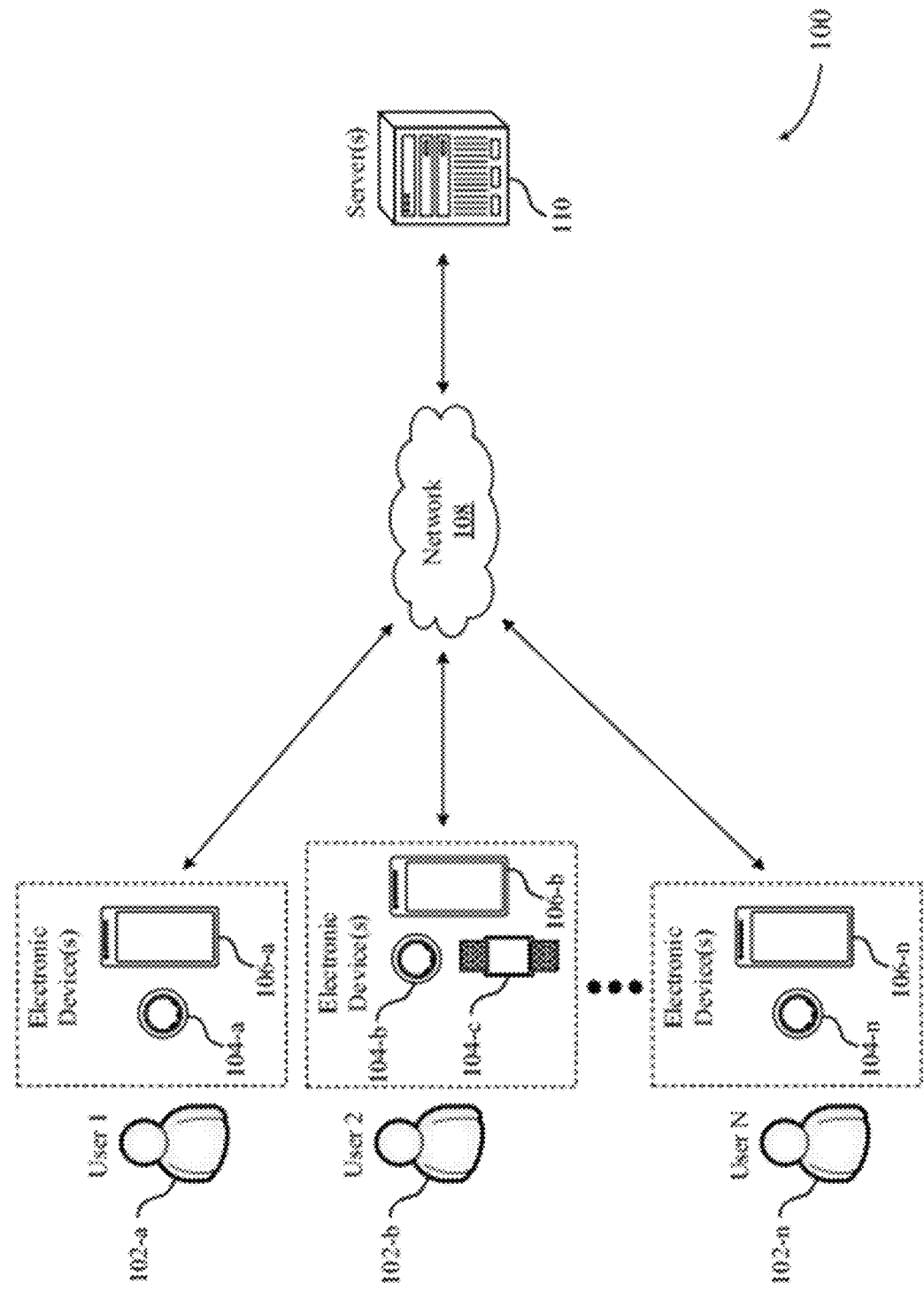
FIG. 1 illustrates an example of a system that supports a wearable device sensor for which measurements may be performed using the devices and methods in accordance with various embodiments of the present disclosure.

An example embodiment and its potential advantages are understood by referring to FIGS. 1 through 9 of the drawings. In this document, like reference signs denote like parts or steps.

Wearable devices may include sensors that measure physiological parameters, such as skin temperature, pulse waveforms, respiratory rate, heart rate, HRV, blood oxygen levels, and the like, of respective users based on detecting light that passes through or reflects through tissue of the user. The physiological parameters may be measured using wearable device sensors that may include one or more light sources that transmit light at a certain wavelength range and one or more light detectors that detect light that has passed or reflected through tissue of the user.

Among other things, a designer of a wearable device sensor needs to make decisions on locations of the light sources and light detectors, number of light sources and light detectors, and wavelengths used in the light sources and light detectors. A challenge is that light can penetrate human tissue differently depending on the wavelength of the light. Further, the physiological structure of the wearable device sensor and for example positioning of the light sources and light detectors in relation to the human tissue can have an influence on the depth of penetration and the amount of light absorbed by the human tissue.

Various embodiments of present disclosure provide a device for measurements for a wearable device sensor. The device may be used for example for test measurements for the purposes of development of the wearable device sensor to help the designer of a wearable device sensor to make decisions on locations of the light sources and light detectors, number of light sources and light detectors, and wavelengths used in the light sources and light detectors. The device of various embodiments of the present disclosure may provide a plurality of measurement results for different human tissue with a plurality of different settings. The measurement results may be used for making conclusions on beneficial decisions in the development of the wearable device sensor.

The device of various example embodiments is based on moving a light source, a light detector, or both, to different measurement positions around a human appendage, such as a wrist, an ankle, an arm, a leg, a finger, a toe, or an ear lobe, to collect information relating to different measurement positions. The light source and the light detector may be moved in synchronization or independently from each other. There may be for example a motor or a manual pivot or some other actuator that causes the movement of the light source, the light detector, or both. The output of the device can be used for studying optical properties of the human appendage. The output of the device may be used for example for the purpose of studying Diffuse Optical Tomography measurements or for studying other measurement methods. The output of the device may be used for optimizing measurement locations of a wearable device sensor and for selecting beneficial wavelengths for the measurements in the wearable device sensor.

In various embodiments, the device may include one or more light sources and one or more light detectors. In an embodiment, both the light source(s) and the light detector(s) work on a wide range of wavelengths. The light source may include light-emitting diodes (LEDs). In some embodiments, the light source emits white light. Additionally or alternatively, the wavelength range of the light source may extend outside visible light wavelengths, e.g. from infrared wavelengths to ultraviolet wavelengths. The light detector may be a spectrometer, which can distinguish intensities of different wavelengths including intensities of different colors. Additionally or alternatively, the light detector may include photosensors, phototransistors, and photodiodes.

In some embodiments, the light source and the light detector may be incorporated in a wearable device and the movement of the light source and the light detector is effected by rotating the wearable device around the human appendage. The wearable device may be rotated by a user or by an external actuator that causes the rotation of the wearable device.

FIG. 1 illustrates an example of a system 100 that supports a wearable device sensor for which measurements may be performed using the devices and methods in accordance with various embodiments of the present disclosure. The system 100 includes a plurality of electronic devices (e.g., wearable devices 104, user devices 106) which may be worn and/or operated by one or more users 102. The system 100 further includes a network 108 and one or more servers 110.

The electronic devices may include any electronic devices known in the art, including wearable devices 104 (e.g., ring wearable devices, watch wearable devices, etc.), user devices 106 (e.g., smartphones, laptops, tablets). The electronic devices associated with the respective users 102 may include one or more of the following functionalities: 1) measuring physiological data, 2) storing the measured data, 3) processing the data, 4) providing outputs (e.g., via GUIs) to a user 102 based on the processed data, and 5) communicating data with one another and/or other computing devices. Different electronic devices may perform one or more of the functionalities.

Example wearable devices 104 may include wearable computing devices, such as a ring computing device (hereinafter "ring") configured to be worn on a user's 102 finger, a wrist computing device (e.g., a smart watch, fitness band, or bracelet) configured to be worn on a user's 102 wrist, and/or a head mounted computing device (e.g., glasses/goggles). Wearable devices 104 may also include bands, straps (e.g., flexible or inflexible bands or straps), stick-on sensors, and the like, which may be positioned in other locations, such as bands around the head (e.g., a forehead headband), arm (e.g., a forearm band and/or bicep band), and/or leg (e.g., a thigh or calf band), behind the ear, under the armpit, and the like. Wearable devices 104 may also be attached to, or included in, articles of clothing. For example, wearable devices 104 may be included in pockets and/or pouches on clothing. As another example, wearable device 104 may be clipped and/or pinned to clothing, or may otherwise be maintained within the vicinity of the user 102. Example articles of clothing may include, but are not limited to, hats, shirts, gloves, pants, socks, outerwear (e.g., jackets), and undergarments. In some implementations, wearable devices 104 may be included with other types of devices such as training/sporting devices that are used during physical activity. For example, wearable devices 104 may be attached to, or included in, a bicycle, skis, a tennis racket, a golf club, and/or training weights.

Much of the present disclosure may be described in the context of a ring wearable device 104. Accordingly, the terms "ring 104," "wearable device 104," and like terms, may be used interchangeably, unless noted otherwise herein. However, the use of the term "ring 104" is not to be regarded as limiting, as it is contemplated herein that aspects of the present disclosure may be performed using other wearable devices (e.g., watch wearable devices, necklace wearable device, bracelet wearable devices, earring wearable devices, anklet wearable devices, and the like).

In some aspects, user devices 106 may include handheld mobile computing devices, such as smartphones and tablet computing devices. User devices 106 may also include personal computers, such as laptop and desktop computing devices. Other example user devices 106 may include server computing devices that may communicate with other electronic devices (e.g., via the Internet). In some implementations, computing devices may include medical devices, such as external wearable computing devices (e.g., Holter monitors). Medical devices may also include implantable medical devices, such as pacemakers and cardioverter defibrillators. Other example user devices 106 may include home computing devices, such as internet of things (IoT) devices (e.g., IoT devices), smart televisions, smart speakers, smart displays (e.g., video call displays), hubs (e.g., wireless communication hubs), security systems, smart appliances (e.g., thermostats and refrigerators), and fitness equipment.

Some electronic devices (e.g., wearable devices 104, user devices 106) may measure physiological parameters of respective users 102, such as photoplethysmography waveforms, continuous skin temperature, a pulse waveform, respiration rate, heart rate, heart rate variability (HRV), actigraphy, galvanic skin response, pulse oximetry, and/or other physiological parameters. Some electronic devices that measure physiological parameters may also perform some/all of the calculations described herein. Some electronic devices may not measure physiological parameters, but may perform some/all of the calculations described herein. For example, a ring (e.g., wearable device 104), mobile device application, or a server computing device may process received physiological data that was measured by other devices.

In some implementations, a user 102 may operate, or may be associated with, multiple electronic devices, some of which may measure physiological parameters and some of which may process the measured physiological parameters. In some implementations, a user 102 may have a ring (e.g., wearable device 104) that measures physiological parameters. The user 102 may also have, or be associated with, a user device 106 (e.g., mobile device, smartphone), where the wearable device 104 and the user device 106 are communicatively coupled to one another. In some cases, the user device 106 may receive data from the wearable device 104 and perform some/all of the calculations described herein. In some implementations, the user device 106 may also measure physiological parameters described herein, such as motion/activity parameters.

For example, as illustrated in FIG. 1, a first user 102-a (User 1) may operate, or may be associated with, a wearable device 104-a (e.g., ring 104-a) and a user device 106-a that may operate as described herein. In this example, the user device 106-a associated with user 102-a may process/store physiological parameters measured by the ring 104-a. Comparatively, a second user 102-b (User 2) may be associated with a ring 104-b, a watch wearable device 104-c (e.g., watch 104-c), and a user device 106-b, where the user device 106-b associated with user 102-b may process/store physiological parameters measured by the ring 104-b and/or the watch 104-c. Moreover, an nth user 102-n (User N) may be associated with an arrangement of electronic devices described herein (e.g., ring 104-n, user device 106-n). In some aspects, wearable devices 104 (e.g., rings 104, watches 104) and other electronic devices may be communicatively coupled to the user devices 106 of the respective users 102 via Bluetooth, Wi-Fi, and other wireless protocols.

In some implementations, the rings 104 (e.g., wearable devices 104) of the system 100 may be configured to collect physiological data from the respective users 102 based on arterial blood flow within the user's finger. In particular, a ring 104 may utilize one or more LEDs (e.g., red LEDs, green LEDs) which emit light on the palm-side of a user's finger to collect physiological data based on arterial blood flow within the user's finger. In some implementations, the ring 104 may acquire the physiological data using a combination of both green and red LEDs. The physiological data may include any physiological data known in the art including, but not limited to, temperature data, accelerometer data (e.g., movement/motion data), heart rate data, HRV data, blood oxygen level data, or any combination thereof.

The use of both green and red LEDs may provide several advantages over other solutions, as red and green LEDs have been found to have their own distinct advantages when acquiring physiological data under different conditions (e.g., light/dark, active/inactive) and via different parts of the body, and the like. For example, green LEDs have been found to exhibit better performance during exercise. Moreover, using multiple LEDs (e.g., green and red LEDs) distributed around the ring 104 has been found to exhibit superior performance as compared to wearable devices which utilize LEDs which are positioned close to one another, such as within a watch wearable device. Furthermore, the blood vessels in the finger (e.g., arteries, capillaries) are more accessible via LEDs as compared to blood vessels in the wrist. In particular, arteries in the wrist are positioned on the bottom of the wrist (e.g., palm-side of the wrist), meaning only capillaries are accessible on the top of the wrist (e.g., back of hand side of the wrist), where wearable watch devices and similar devices are typically worn. As such, utilizing LEDs and other sensors within a ring 104 has been found to exhibit superior performance as compared to wearable devices worn on the wrist, as the ring 104 may have greater access to arteries (as compared to capillaries), thereby resulting in stronger signals and more valuable physiological data.

The electronic devices of the system 100 (e.g., user devices 106, wearable devices 104) may be communicatively coupled to one or more servers 110 via wired or wireless communication protocols. For example, as shown in FIG. 1, the electronic devices (e.g., user devices 106) may be communicatively coupled to one or more servers 110 via a network 108. The network 108 may implement transfer control protocol and internet protocol (TCP/IP), such as the Internet, or may implement other network 108 protocols. Network connections between the network 108 and the respective electronic devices may facilitate transport of data via email, web, text messages, mail, or any other appropriate form of interaction within a computer network 108. For example, in some implementations, the ring 104-*a* associated with the first user 102-*a* may be communicatively coupled to the user device 106-*a*, where the user device 106-*a* is communicatively coupled to the servers 110 via the network 108. In additional or alternative cases, wearable devices 104 (e.g., rings 104, watches 104) may be directly communicatively coupled to the network 108.

The system 100 may offer an on-demand database service between the user devices 106 and the one or more servers 110. In some cases, the servers 110 may receive data from the user devices 106 via the network 108, and may store and analyze the data. Similarly, the servers 110 may provide data to the user devices 106 via the network 108. In some cases, the servers 110 may be located at one or more data centers. The servers 110 may be used for data storage, management, and processing. In some implementations, the servers 110 may provide a web-based interface to the user device 106 via web browsers.

In some implementations, the system 100 may detect periods of time during which a user 102 is asleep, and classify periods of time during which the user 102 is asleep into one or more sleep stages (e.g., sleep stage classification). For example, as shown in FIG. 1, User 102-*a* may be associated with a wearable device 104-*a* (e.g., ring 104-*a*) and a user device 106-*a*. In this example, the ring 104-*a* may collect physiological data associated with the user 102-*a*, including temperature, heart rate, HRV, respiratory rate, and the like. In some aspects, data collected by the ring 104-*a* may be input to a machine learning classifier, where the machine learning classifier is configured to determine periods of time during which the user 102-*a* is (or was) asleep. Moreover, the machine learning classifier may be configured to classify periods of time into different sleep stages, including an awake sleep stage, a rapid eye movement (REM) sleep stage, a light sleep stage (non-REM (NREM)), and a deep sleep stage (NREM). In some aspects, the classified sleep stages may be displayed to the user 102-*a* via a GUI of the user device 106-*a*. Sleep stage classification may be used to provide feedback to a user 102-*a* regarding the user's sleeping patterns, such as recommended bedtimes, recommended wake-up times, and the like. Moreover, in some implementations, sleep stage classification techniques described herein may be used to calculate scores for the respective user, such as Sleep Scores, Readiness Scores, and the like.

In some implementations, the system 100 may utilize circadian rhythm-derived features to further improve physiological data collection, data processing procedures, and other techniques described herein. The term circadian rhythm may refer to a natural, internal process that regulates an individual's sleep-wake cycle, which repeats approximately every 24 hours. In this regard, techniques described herein may utilize circadian rhythm adjustment models to improve physiological data collection, analysis, and data processing. For example, a circadian rhythm adjustment model may be input into a machine learning classifier along with physiological data collected from the user 102-*a* via the wearable device 104-*a*. In this example, the circadian rhythm adjustment model may be configured to "weight," or adjust, physiological data collected throughout a user's natural, approximately 24-hour circadian rhythm. In some implementations, the system may initially start with a "baseline" circadian rhythm adjustment model, and may modify the baseline model using physiological data collected from each user 102 to generate tailored, individualized circadian rhythm adjustment models which are specific to each respective user 102.

In some implementations, the system 100 may utilize other biological rhythms to further improve physiological data collection, analysis, and processing by phase of these other rhythms. For example, if a weekly rhythm is detected within an individual's baseline data, then the model may be configured to adjust "weights" of data by day of the week. Biological rhythms that may require adjustment to the model by this method include: 1) ultradian (faster than a day rhythms, including sleep cycles in a sleep state, and oscillations from less than an hour to several hours periodicity in the measured physiological variables during wake state; 2) circadian rhythms; 3) non-endogenous daily rhythms shown to be imposed on top of circadian rhythms, as in work schedules; 4) weekly rhythms, or other artificial time periodicities exogenously imposed (e.g. in a hypothetical culture with 12 day "weeks", 12 day rhythms could be used); 5) multi-day ovarian rhythms in women and spermatogenesis rhythms in men; 6) lunar rhythms (relevant for individuals living with low or no artificial lights); and 7) seasonal rhythms.

The biological rhythms are not always stationary rhythms. For example, many women experience variability in ovarian cycle length across cycles, and ultradian rhythms are not expected to occur at exactly the same time or periodicity across days even within a user. As such, signal processing techniques sufficient to quantify the frequency composition while preserving temporal resolution of these rhythms in physiological data may be used to improve detection of these rhythms, to assign phase of each rhythm to each moment in time measured, and to thereby modify adjustment models and comparisons of time intervals. The biological rhythm-adjustment models and parameters can be added in linear or non-linear combinations as appropriate to more accurately capture the dynamic physiological baselines of an individual or group of individuals.

Figure 2:
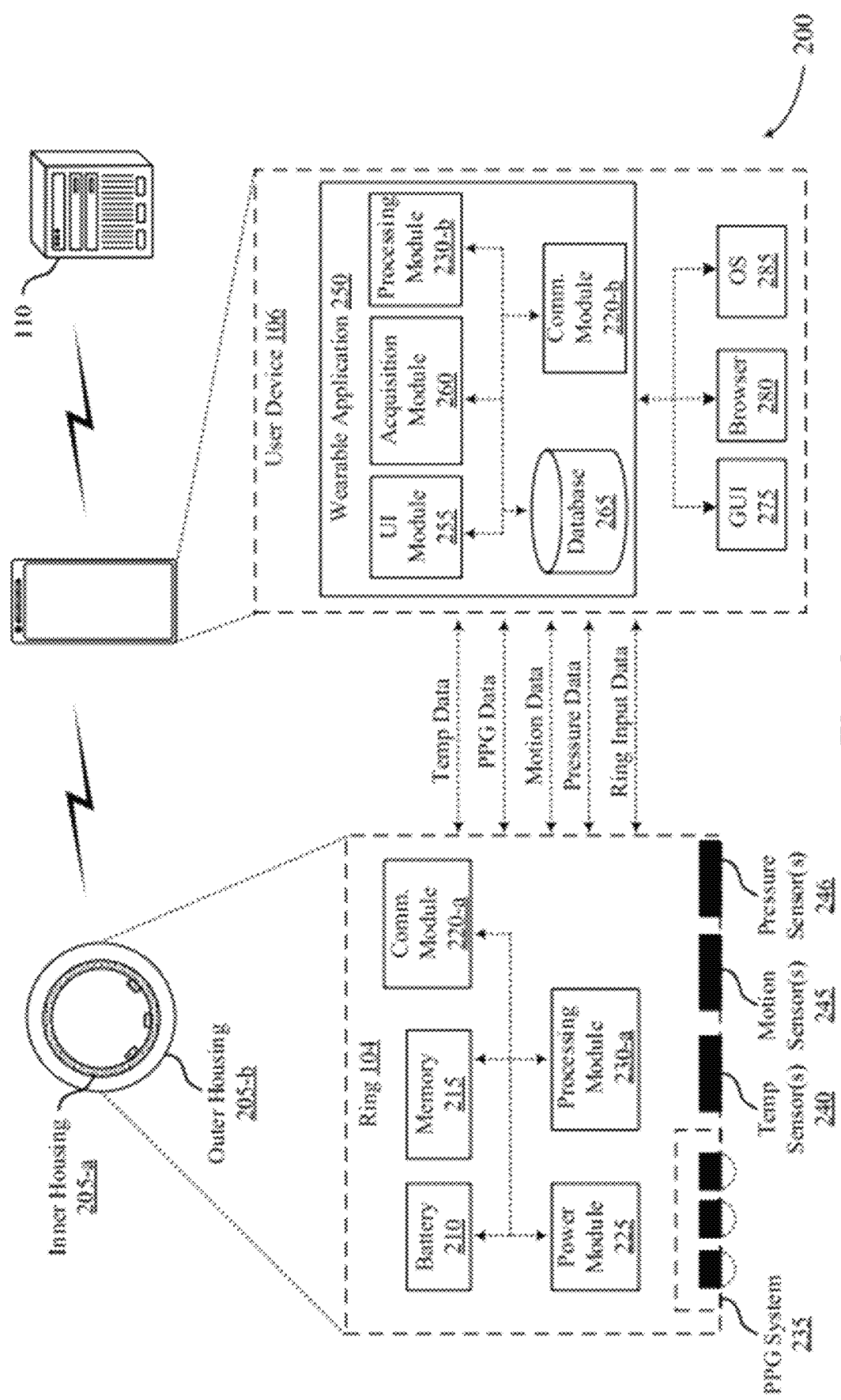
FIG. 2 illustrates an example of a system that supports a wearable device sensor for which measurements may be performed using the devices and methods in accordance with various embodiments of the present disclosure.

FIG. 2 illustrates an example of a system 200 that supports a wearable device for which measurements may be performed using the devices and methods in accordance with various embodiments of the present disclosure. The system 200 may implement, or be implemented by, system 100. In particular, system 200 illustrates an example of a ring 104 (e.g., wearable device 104), a user device 106, and a server 110, as described with reference to FIG. 1.

In some cases, the ring 104 may be configured to be worn around a user's finger, and may determine one or more user physiological parameters when worn around the user's finger. Example measurements and determinations may include, but are not limited to, user skin temperature, pulse waveforms, respiratory rate, heart rate, HRV, blood oxygen levels, and the like.

The system 200 further comprises a user device 106 (e.g., a smartphone) in communication with the ring 104. For example, the ring 104 may be in wireless and/or wired communication with the user device 106. In some implementations, the ring 104 may send measured and processed data (e.g., temperature data, photoplethysmogram (PPG)

data, motion/accelerometer data, ring input data, and the like) to the user device 106. The user device 106 may also send data to the ring 104, such as ring 104 firmware/configuration updates. The user device 106 may process data. In some implementations, the user device 106 may transmit data to the server 110 for processing and/or storage.

The ring 104 may include a housing 205 that may include an inner housing 205-a and an outer housing 205-b. In some aspects, the housing 205 of the ring 104 may store or otherwise include various components of the ring including, but not limited to, device electronics, a power source (e.g., battery 210, and/or capacitor), one or more substrates (e.g., printable circuit boards) that interconnect the device electronics and/or power source, and the like. The device electronics may include device modules (e.g., hardware/software), such as: a processing module 230-a, a memory 215, a communication module 220-a, a power module 225, and the like. The device electronics may also include one or more sensors. Example sensors may include one or more temperature sensors 240, a PPG sensor assembly (e.g., PPG system 235), and one or more motion sensors 245.

The sensors may include associated modules (not illustrated) configured to communicate with the respective components/modules of the ring 104, and generate signals associated with the respective sensors. In some aspects, each of the components/modules of the ring 104 may be communicatively coupled to one another via wired or wireless connections. Moreover, the ring 104 may include additional and/or alternative sensors or other components that are configured to collect physiological data from the user, including light sensors (e.g., LEDs), oximeters, and the like.

The ring 104 shown and described with reference to FIG. 2 is provided solely for illustrative purposes. As such, the ring 104 may include additional or alternative components as those illustrated in FIG. 2. Other rings 104 that provide functionality described herein may be fabricated. For example, rings 104 with fewer components (e.g., sensors) may be fabricated. In a specific example, a ring 104 with a single temperature sensor 240 (or other sensor), a power source, and device electronics configured to read the single temperature sensor 240 (or other sensor) may be fabricated. In another specific example, a temperature sensor 240 (or other sensor) may be attached to a user's finger (e.g., using a clamps, spring loaded clamps, etc.). In this case, the sensor may be wired to another computing device, such as a wrist worn computing device that reads the temperature sensor 240 (or other sensor). In other examples, a ring 104 that includes additional sensors and processing functionality may be fabricated.

The housing 205 may include one or more housing 205 components. The housing 205 may include an outer housing 205-b component (e.g., a shell) and an inner housing 205-a component (e.g., a molding). The housing 205 may include additional components (e.g., additional layers) not explicitly illustrated in FIG. 2. For example, in some implementations, the ring 104 may include one or more insulating layers that electrically insulate the device electronics and other conductive materials (e.g., electrical traces) from the outer housing 205-b (e.g., a metal outer housing 205-b). The housing 205 may provide structural support for the device electronics, battery 210, substrate(s), and other components. For example, the housing 205 may protect the device electronics, battery 210, and substrate(s) from mechanical forces, such as pressure and impacts. The housing 205 may also protect the device electronics, battery 210, and substrate(s) from water and/or other chemicals.

The outer housing 205-b may be fabricated from one or more materials. In some implementations, the outer housing 205-b may include a metal, such as titanium, that may provide strength and abrasion resistance at a relatively light weight. The outer housing 205-b may also be fabricated from other materials, such polymers. In some implementations, the outer housing 205-b may be protective as well as decorative.

The inner housing 205-a may be configured to interface with the user's finger. The inner housing 205-a may be formed from a polymer (e.g., a medical grade polymer) or other material. In some implementations, the inner housing 205-a may be transparent. For example, the inner housing 205-a may be transparent to light emitted by the PPG light emitting diodes (LEDs). In some implementations, the inner housing 205-a component may be molded onto the outer housing 205-b. For example, the inner housing 205-a may include a polymer that is molded (e.g., injection molded) to fit into an outer housing 205-b metallic shell.

The ring 104 may include one or more substrates (not illustrated). The device electronics and battery 210 may be included on the one or more substrates. For example, the device electronics and battery 210 may be mounted on one or more substrates. Example substrates may include one or more printed circuit boards (PCBs), such as flexible PCB (e.g., polyimide). In some implementations, the electronics/battery 210 may include surface mounted devices (e.g., surface-mount technology (SMT) devices) on a flexible PCB. In some implementations, the one or more substrates (e.g., one or more flexible PCBs) may include electrical traces that provide electrical communication between device electronics. The electrical traces may also connect the battery 210 to the device electronics.

The device electronics, battery 210, and substrates may be arranged in the ring 104 in a variety of ways. In some implementations, one substrate that includes device electronics may be mounted along the bottom of the ring 104 (e.g., the bottom half), such that the sensors (e.g., PPG system 235, temperature sensors 240, motion sensors 245, and other sensors) interface with the underside of the user's finger. In these implementations, the battery 210 may be included along the top portion of the ring 104 (e.g., on another substrate).

The various components/modules of the ring 104 represent functionality (e.g., circuits and other components) that may be included in the ring 104. Modules may include any discrete and/or integrated electronic circuit components that implement analog and/or digital circuits capable of producing the functions attributed to the modules herein. For example, the modules may include analog circuits (e.g., amplification circuits, filtering circuits, analog/digital conversion circuits, and/or other signal conditioning circuits). The modules may also include digital circuits (e.g., combinational or sequential logic circuits, memory circuits etc.).

The memory 215 (memory module) of the ring 104 may include any volatile, non-volatile, magnetic, or electrical media, such as a random access memory (RAM), read-only memory (ROM), non-volatile RAM (NVRAM), electrically-erasable programmable ROM (EEPROM), flash memory, or any other memory device. The memory 215 may store any of the data described herein. For example, the memory 215 may be configured to store data (e.g., motion data, temperature data, PPG data) collected by the respective sensors and PPG system 235. Furthermore, memory 215 may include instructions that, when executed by one or more processing circuits, cause the modules to perform various functions attributed to the modules herein. The device electronics of the ring 104 described herein are only example device electronics. As such, the types of electronic components used to implement the device electronics may vary based on design considerations.

The functions attributed to the modules of the ring 104 described herein may be embodied as one or more processors, hardware, firmware, software, or any combination thereof. Depiction of different features as modules is intended to highlight different functional aspects and does not necessarily imply that such modules must be realized by separate hardware/software components. Rather, functionality associated with one or more modules may be performed by separate hardware/software components or integrated within common hardware/software components.

The processing module 230-*a* of the ring 104 may include one or more processors (e.g., processing units), microcontrollers, digital signal processors, systems on a chip (SOCs), and/or other processing devices. The processing module 230-*a* communicates with the modules included in the ring 104. For example, the processing module 230-*a* may transmit/receive data to/from the modules and other components of the ring 104, such as the sensors. As described herein, the modules may be implemented by various circuit components. Accordingly, the modules may also be referred to as circuits (e.g., a communication circuit and power circuit).

The processing module 230-*a* may communicate with the memory 215. The memory 215 may include computer-readable instructions that, when executed by the processing module 230-*a*, cause the processing module 230-*a* to perform the various functions attributed to the processing module 230-*a* herein. In some implementations, the processing module 230-*a* (e.g., a microcontroller) may include additional features associated with other modules, such as communication functionality provided by the communication module 220-*a* (e.g., an integrated Bluetooth Low Energy transceiver) and/or additional onboard memory 215.

The communication module 220-*a* may include circuits that provide wireless and/or wired communication with the user device 106 (e.g., communication module 220-*b* of the user device 106). In some implementations, the communication modules 220-*a*, 220-*b* may include wireless communication circuits, such as Bluetooth circuits and/or Wi-Fi circuits. In some implementations, the communication modules 220-*a*, 220-*b* can include wired communication circuits, such as Universal Serial Bus (USB) communication circuits. Using the communication module 220-*a*, the ring 104 and the user device 106 may be configured to communicate with each other. The processing module 230-*a* of the ring may be configured to transmit/receive data to/from the user device 106 via the communication module 220-*a*. Example data may include, but is not limited to, motion data, temperature data, pulse waveforms, heart rate data, HRV data, PPG data, and status updates (e.g., charging status, battery charge level, and/or ring 104 configuration settings). The processing module 230-*a* of the ring may also be configured to receive updates (e.g., software/firmware updates) and data from the user device 106.

The ring 104 may include a battery 210 (e.g., a rechargeable battery 210). An example battery 210 may include a Lithium-Ion or Lithium-Polymer type battery 210, although a variety of battery 210 options are possible. The battery 210 may be wirelessly charged. In some implementations, the ring 104 may include a power source other than the battery 210, such as a capacitor. The power source (e.g., battery 210 or capacitor) may have a curved geometry that matches the curve of the ring 104. In some aspects, a charger or other power source may include additional sensors that may be used to collect data in addition to, or that supplements, data collected by the ring 104 itself. Moreover, a charger or other power source for the ring 104 may function as a user device 106, in which case the charger or other power source for the ring 104 may be configured to receive data from the ring 104, store and/or process data received from the ring 104, and communicate data between the ring 104 and the servers 110.

In some aspects, the ring 104 includes a power module 225 that may control charging of the battery 210. For example, the power module 225 may interface with an external wireless charger that charges the battery 210 when interfaced with the ring 104. The charger may include a datum structure that mates with a ring 104 datum structure to create a specified orientation with the ring 104 during 104 charging. The power module 225 may also regulate voltage (s) of the device electronics, regulate power output to the device electronics, and monitor the state of charge of the battery 210. In some implementations, the battery 210 may include a protection circuit module (PCM) that protects the battery 210 from high current discharge, over voltage during 104 charging, and under voltage during 104 discharge. The power module 225 may also include electro-static discharge (ESD) protection.

The one or more temperature sensors 240 may be electrically coupled to the processing module 230-*a*. The temperature sensor 240 may be configured to generate a temperature signal (e.g., temperature data) that indicates a temperature read or sensed by the temperature sensor 240. The processing module 230-*a* may determine a temperature of the user in the location of the temperature sensor 240. For example, in the ring 104, temperature data generated by the temperature sensor 240 may indicate a temperature of a user at the user's finger (e.g., skin temperature). In some implementations, the temperature sensor 240 may contact the user's skin. In other implementations, a portion of the housing 205 (e.g., the inner housing 205-*a*) may form a barrier (e.g., a thin, thermally conductive barrier) between the temperature sensor 240 and the user's skin. In some implementations, portions of the ring 104 configured to contact the user's finger may have thermally conductive portions and thermally insulative portions. The thermally conductive portions may conduct heat from the user's finger to the temperature sensors 240. The thermally insulative portions may insulate portions of the ring 104 (e.g., the temperature sensor 240) from ambient temperature.

In some implementations, the temperature sensor 240 may generate a digital signal (e.g., temperature data) that the processing module 230-*a* may use to determine the temperature. As another example, in cases where the temperature sensor 240 includes a passive sensor, the processing module 230-*a* (or a temperature sensor 240 module) may measure a current/voltage generated by the temperature sensor 240 and determine the temperature based on the measured current/voltage. Example temperature sensors 240 may include a thermistor, such as a negative temperature coefficient (NTC) thermistor, or other types of sensors including resistors, transistors, diodes, and/or other electrical/electronic components.

The processing module 230-*a* may sample the user's temperature over time. For example, the processing module 230-*a* may sample the user's temperature according to a sampling rate. An example sampling rate may include one sample per second, although the processing module 230-*a* may be configured to sample the temperature signal at other sampling rates that are higher or lower than one sample per second. In some implementations, the processing module 230-a may sample the user's temperature continuously throughout the day and night. Sampling at a sufficient rate (e.g., one sample per second) throughout the day may provide sufficient temperature data for analysis described herein.

The processing module 230-a may store the sampled temperature data in memory 215. In some implementations, the processing module 230-a may process the sampled temperature data. For example, the processing module 230-a may determine average temperature values over a period of time. In one example, the processing module 230-a may determine an average temperature value each minute by summing all temperature values collected over the minute and dividing by the number of samples over the minute. In a specific example where the temperature is sampled at one sample per second, the average temperature may be a sum of all sampled temperatures for one minute divided by sixty seconds. The memory 215 may store the average temperature values over time. In some implementations, the memory 215 may store average temperatures (e.g., one per minute) instead of sampled temperatures in order to conserve memory 215.

The sampling rate, which may be stored in memory 215, may be configurable. In some implementations, the sampling rate may be the same throughout the day and night. In other implementations, the sampling rate may be changed throughout the day/night. In some implementations, the ring 104 may filter/reject temperature readings, such as large spikes in temperature that are not indicative of physiological changes (e.g., a temperature spike from a hot shower). In some implementations, the ring 104 may filter/reject temperature readings that may not be reliable due to other factors, such as excessive motion during 104 exercise (e.g., as indicated by a motion sensor 245).

The ring 104 (e.g., communication module) may transmit the sampled and/or average temperature data to the user device 106 for storage and/or further processing. The user device 106 may transfer the sampled and/or average temperature data to the server 110 for storage and/or further processing.

Although the ring 104 is illustrated as including a single temperature sensor 240, the ring 104 may include multiple temperature sensors 240 in one or more locations, such as arranged along the inner housing 205-a near the user's finger. In some implementations, the temperature sensors 240 may be stand-alone temperature sensors 240. Additionally, or alternatively, one or more temperature sensors 240 may be included with other components (e.g., packaged with other components), such as with the accelerometer and/or processor.

The processing module 230-a may acquire and process data from multiple temperature sensors 240 in a similar manner described with respect to a single temperature sensor 240. For example, the processing module 230 may individually sample, average, and store temperature data from each of the multiple temperature sensors 240. In other examples, the processing module 230-a may sample the sensors at different rates and average/store different values for the different sensors. In some implementations, the processing module 230-a may be configured to determine a single temperature based on the average of two or more temperatures determined by two or more temperature sensors 240 in different locations on the finger.

The temperature sensors 240 on the ring 104 may acquire distal temperatures at the user's finger (e.g., any finger). For example, one or more temperature sensors 240 on the ring 104 may acquire a user's temperature from the underside of a finger or at a different location on the finger. In some implementations, the ring 104 may continuously acquire distal temperature (e.g., at a sampling rate). Although distal temperature measured by a ring 104 at the finger is described herein, other devices may measure temperature at the same/different locations. In some cases, the distal temperature measured at a user's finger may differ from the temperature measured at a user's wrist or other external body location. Additionally, the distal temperature measured at a user's finger (e.g., a "shell" temperature) may differ from the user's core temperature. As such, the ring 104 may provide a useful temperature signal that may not be acquired at other internal/external locations of the body. In some cases, continuous temperature measurement at the finger may capture temperature fluctuations (e.g., small or large fluctuations) that may not be evident in core temperature. For example, continuous temperature measurement at the finger may capture minute-to-minute or hour-to-hour temperature fluctuations that provide additional insight that may not be provided by other temperature measurements elsewhere in the body.

The ring 104 may include a PPG system 235. The PPG system 235 may include one or more optical transmitters that transmit light. The PPG system 235 may also include one or more optical receivers that receive light transmitted by the one or more optical transmitters. An optical receiver may generate a signal (hereinafter "PPG" signal) that indicates an amount of light received by the optical receiver. The optical transmitters may illuminate a region of the user's finger. The PPG signal generated by the PPG system 235 may indicate the perfusion of blood in the illuminated region. For example, the PPG signal may indicate blood volume changes in the illuminated region caused by a user's pulse pressure. The processing module 230-a may sample the PPG signal and determine a user's pulse waveform based on the PPG signal. The processing module 230-a may determine a variety of physiological parameters based on the user's pulse waveform, such as a user's respiratory rate, heart rate, HRV, oxygen saturation, and other circulatory parameters.

In some implementations, the PPG system 235 may be configured as a reflective PPG system 235 where the optical receiver(s) receive transmitted light that is reflected through the region of the user's finger. In some implementations, the PPG system 235 may be configured as a transmissive PPG system 235 where the optical transmitter(s) and optical receiver(s) are arranged opposite to one another, such that light is transmitted directly through a portion of the user's finger to the optical receiver(s).

The number and ratio of transmitters and receivers included in the PPG system 235 may vary. Example optical transmitters may include light-emitting diodes (LEDs). The optical transmitters may transmit light in the infrared spectrum and/or other spectrums. Example optical receivers may include, but are not limited to, photosensors, phototransistors, and photodiodes. The optical receivers may be configured to generate PPG signals in response to the wavelengths received from the optical transmitters. The location of the transmitters and receivers may vary. Additionally, a single device may include reflective and/or transmissive PPG systems 235.

The PPG system 235 illustrated in FIG. 2 may include a reflective PPG system 235 in some implementations. In these implementations, the PPG system 235 may include a centrally located optical receiver (e.g., at the bottom of the ring 104) and two optical transmitters located on each side of the optical receiver. In this implementation, the PPG system 235 (e.g., optical receiver) may generate the PPG signal based on light received from one or both of the optical transmitters. In other implementations, other placements, combinations, and/or configurations of one or more optical transmitters and/or optical receivers are contemplated.

The processing module 230-a may control one or both of the optical transmitters to transmit light while sampling the PPG signal generated by the optical receiver. In some implementations, the processing module 230-a may cause the optical transmitter with the stronger received signal to transmit light while sampling the PPG signal generated by the optical receiver. For example, the selected optical transmitter may continuously emit light while the PPG signal is sampled at a sampling rate (e.g., 250 Hz).

Sampling the PPG signal generated by the PPG system 235 may result in a pulse waveform that may be referred to as a "PPG." The pulse waveform may indicate blood pressure vs time for multiple cardiac cycles. The pulse waveform may include peaks that indicate cardiac cycles. Additionally, the pulse waveform may include respiratory induced variations that may be used to determine respiration rate. The processing module 230-a may store the pulse waveform in memory 215 in some implementations. The processing module 230-a may process the pulse waveform as it is generated and/or from memory 215 to determine user physiological parameters described herein.

The processing module 230-a may determine the user's heart rate based on the pulse waveform. For example, the processing module 230-a may determine heart rate (e.g., in beats per minute) based on the time between peaks in the pulse waveform. The time between peaks may be referred to as an interbeat interval (IBI). The processing module 230-a may store the determined heart rate values and IBI values in memory 215.

The processing module 230-a may determine HRV over time. For example, the processing module 230-a may determine HRV based on the variation in the IBIs. The processing module 230-a may store the HRV values over time in the memory 215. Moreover, the processing module 230-a may determine the user's respiratory rate over time. For example, the processing module 230-a may determine respiratory rate based on frequency modulation, amplitude modulation, or baseline modulation of the user's IBI values over a period of time. Respiratory rate may be calculated in breaths per minute or as another breathing rate (e.g., breaths per 30 seconds). The processing module 230-a may store user respiratory rate values over time in the memory 215.

The ring 104 may include one or more motion sensors 245, such as one or more accelerometers (e.g., 6-D accelerometers) and/or one or more gyroscopes (gyros). The motion sensors 245 may generate motion signals that indicate motion of the sensors. For example, the ring 104 may include one or more accelerometers that generate acceleration signals that indicate acceleration of the accelerometers. As another example, the ring 104 may include one or more gyro sensors that generate gyro signals that indicate angular motion (e.g., angular velocity) and/or changes in orientation. The motion sensors 245 may be included in one or more sensor packages. An example accelerometer/gyro sensor is a Bosch BMI160 inertial micro electro-mechanical system (MEMS) sensor that may measure angular rates and accelerations in three perpendicular axes.

The processing module 230-a may sample the motion signals at a sampling rate (e.g., 50 Hz) and determine the motion of the ring 104 based on the sampled motion signals. For example, the processing module 230-a may sample acceleration signals to determine acceleration of the ring 104. As another example, the processing module 230-a may sample a gyro signal to determine angular motion. In some implementations, the processing module 230-a may store motion data in memory 215. Motion data may include sampled motion data as well as motion data that is calculated based on the sampled motion signals (e.g., acceleration and angular values).

The ring 104 may store a variety of data described herein. For example, the ring 104 may store temperature data, such as raw sampled temperature data and calculated temperature data (e.g., average temperatures). As another example, the ring 104 may store PPG signal data, such as pulse waveforms and data calculated based on the pulse waveforms (e.g., heart rate values, IBI values, HRV values, and respiratory rate values). The ring 104 may also store motion data, such as sampled motion data that indicates linear and angular motion.

The ring 104, or other computing device, may calculate and store additional values based on the sampled/calculated physiological data. For example, the processing module 230 may calculate and store various metrics, such as sleep metrics (e.g., a Sleep Score), activity metrics, and readiness metrics. In some implementations, additional values/metrics may be referred to as "derived values." The ring 104, or other computing/wearable device, may calculate a variety of values/metrics with respect to motion. Example derived values for motion data may include, but are not limited to, motion count values, regularity values, intensity values, metabolic equivalence of task values (METs), and orientation values. Motion counts, regularity values, intensity values, and METs may indicate an amount of user motion (e.g., velocity/acceleration) over time. Orientation values may indicate how the ring 104 is oriented on the user's finger and if the ring 104 is worn on the left hand or right hand.

In some implementations, motion counts and regularity values may be determined by counting a number of acceleration peaks within one or more periods of time (e.g., one or more 30 second to 1 minute periods). Intensity values may indicate a number of movements and the associated intensity (e.g., acceleration values) of the movements. The intensity values may be categorized as low, medium, and high, depending on associated threshold acceleration values. METs may be determined based on the intensity of movements during a period of time (e.g., 30 seconds), the regularity/irregularity of the movements, and the number of movements associated with the different intensities.

In some implementations, the processing module 230-a may compress the data stored in memory 215. For example, the processing module 230-a may delete sampled data after making calculations based on the sampled data. As another example, the processing module 230-a may average data over longer periods of time in order to reduce the number of stored values. In a specific example, if average temperatures for a user over one minute are stored in memory 215, the processing module 230-a may calculate average temperatures over a five minute time period for storage, and then subsequently erase the one minute average temperature data. The processing module 230-a may compress data based on a variety of factors, such as the total amount of used/available memory 215 and/or an elapsed time since the ring 104 last transmitted the data to the user device 106.

Although a user's physiological parameters may be measured by sensors included on a ring 104, other devices may measure a user's physiological parameters. For example, although a user's temperature may be measured by a temperature sensor 240 included in a ring 104, other devices may measure a user's temperature. In some examples, other wearable devices (e.g., wrist devices) may include sensors that measure user physiological parameters. Additionally, medical devices, such as external medical devices (e.g., wearable medical devices) and/or implantable medical devices, may measure a user's physiological parameters. One or more sensors on any type of computing device may be used to implement the techniques described herein.

The physiological measurements may be taken continuously throughout the day and/or night. In some implementations, the physiological measurements may be taken during 104 portions of the day and/or portions of the night. In some implementations, the physiological measurements may be taken in response to determining that the user is in a specific state, such as an active state, resting state, and/or a sleeping state. For example, the ring 104 can make physiological measurements in a resting/sleep state in order to acquire cleaner physiological signals. In one example, the ring 104 or other device/system may detect when a user is resting and/or sleeping and acquire physiological parameters (e.g., temperature) for that detected state. The devices/systems may use the resting/sleep physiological data and/or other data when the user is in other states in order to implement the techniques of the present disclosure.

In some implementations, as described previously herein, the ring 104 may be configured to collect, store, and/or process data, and may transfer any of the data described herein to the user device 106 for storage and/or processing. In some aspects, the user device 106 includes a wearable application 250, an operating system (OS), a web browser application (e.g., web browser 280), one or more additional applications, and a GUI 275. The user device 106 may further include other modules and components, including sensors, audio devices, haptic feedback devices, and the like. The wearable application 250 may include an example of an application (e.g., "app") that may be installed on the user device 106. The wearable application 250 may be configured to acquire data from the ring 104, store the acquired data, and process the acquired data as described herein. For example, the wearable application 250 may include a user interface (UI) module 255, an acquisition module 260, a processing module 230-b, a communication module 220-b, and a storage module (e.g., database 265) configured to store application data.

The various data processing operations described herein may be performed by the ring 104, the user device 106, the servers 110, or any combination thereof. For example, in some cases, data collected by the ring 104 may be pre-processed and transmitted to the user device 106. In this example, the user device 106 may perform some data processing operations on the received data, may transmit the data to the servers 110 for data processing, or both. For instance, in some cases, the user device 106 may perform processing operations that require relatively low processing power and/or operations that require a relatively low latency, whereas the user device 106 may transmit the data to the servers 110 for processing operations that require relatively high processing power and/or operations that may allow relatively higher latency.

In some cases, the ring 104, user device 106, and server 110 of the system 200 may be configured to evaluate sleep patterns for a user. In particular, the respective components of the system 200 may be used to collect data from a user via the ring 104, and generate one or more scores (e.g., Sleep Score, Readiness Score) for the user based on the collected data. For example, as noted previously herein, the ring 104 of the system 200 may be worn by a user to collect data from the user, including temperature, heart rate, HRV, and the like. Data collected by the ring 104 may be used to determine when the user is asleep in order to evaluate the user's sleep for a given "sleep day." In some aspects, scores may be calculated for the user for each respective sleep day, such that a first sleep day is associated with a first set of scores, and a second sleep day is associated with a second set of scores. Scores may be calculated for each respective sleep day based on data collected by the ring 104 during the respective sleep day. Scores may include, but are not limited to, Sleep Scores, Readiness Scores, and the like.

In some cases, "sleep days" may align with the traditional calendar days, such that a given sleep day runs from midnight to midnight of the respective calendar day. In other cases, sleep days may be offset relative to calendar days. For example, sleep days may run from 6:00 pm (18:00) of a calendar day until 6:00 pm (18:00) of the subsequent calendar day. In this example, 6:00 pm may serve as a "cut-off time," where data collected from the user before 6:00 pm is counted for the current sleep day, and data collected from the user after 6:00 pm is counted for the subsequent sleep day. Due to the fact that most individuals sleep the most at night, offsetting sleep days relative to calendar days may enable the system 200 to evaluate sleep patterns for users in such a manner that is consistent with their sleep schedules. In some cases, users may be able to selectively adjust (e.g., via the GUI) a timing of sleep days relative to calendar days so that the sleep days are aligned with the duration of time that the respective users typically sleep.

In some implementations, each overall score for a user for each respective day (e.g., Sleep Score, Readiness Score) may be determined/calculated based on one or more "contributors," "factors," or "contributing factors." For example, a user's overall Sleep Score may be calculated based on a set of contributors, including: total sleep, efficiency, restfulness, REM sleep, deep sleep, latency, timing, or any combination thereof. The Sleep Score may include any quantity of contributors. The "total sleep" contributor may refer to the sum of all sleep periods of the sleep day. The "efficiency" contributor may reflect the percentage of time spent asleep compared to time spent awake while in bed, and may be calculated using the efficiency average of long sleep periods (e.g., primary sleep period) of the sleep day, weighted by a duration of each sleep period. The "restfulness" contributor may indicate how restful the user's sleep is, and may be calculated using the average of all sleep periods of the sleep day, weighted by a duration of each period. The restfulness contributor may be based on a "wake up count" (e.g., sum of all the wake-ups (when user wakes up) detected during different sleep periods), excessive movement, and a "got up count" (e.g., sum of all the got-ups (when user gets out of bed) detected during the different sleep periods).

The "REM sleep" contributor may refer to a sum total of REM sleep durations across all sleep periods of the sleep day including REM sleep. Similarly, the "deep sleep" contributor may refer to a sum total of deep sleep durations across all sleep periods of the sleep day including deep sleep. The "latency" contributor may signify how long (e.g., average, median, longest) the user takes to go to sleep, and may be calculated using the average of long sleep periods throughout the sleep day, weighted by a duration of each period and the number of such periods (e.g., consolidation of a given sleep stage or sleep stages may be its own contributor or weight other contributors). Lastly, the "timing" contributor may refer to a relative timing of sleep periods within the sleep day and/or calendar day, and may be calculated using the average of all sleep periods of the sleep day, weighted by a duration of each period.

By way of another example, a user's overall Readiness Score may be calculated based on a set of contributors, including: sleep, sleep balance, heart rate, HRV balance, recovery index, temperature, activity, activity balance, or any combination thereof. The Readiness Score may include any quantity of contributors. The "sleep" contributor may refer to the combined Sleep Score of all sleep periods within the sleep day. The "sleep balance" contributor may refer to a cumulative duration of all sleep periods within the sleep day. In particular, sleep balance may indicate to a user whether the sleep that the user has been getting over some duration of time (e.g., the past two weeks) is in balance with the user's needs. Typically, adults need 7-9 hours of sleep a night to stay healthy, alert, and to perform at their best both mentally and physically. However, it is normal to have an occasional night of bad sleep, so the sleep balance contributor takes into account long-term sleep patterns to determine whether each user's sleep needs are being met. The "resting heart rate" contributor may indicate a lowest heart rate from the longest sleep period of the sleep day (e.g., primary sleep period) and/or the lowest heart rate from naps occurring after the primary sleep period.

Continuing with reference to the "contributors" (e.g., factors, contributing factors) of the Readiness Score, the "HRV balance" contributor may indicate a highest HRV average from the primary sleep period and the naps happening after the primary sleep period. The HRV balance contributor may help users keep track of their recovery status by comparing their HRV trend over a first time period (e.g., two weeks) to an average HRV over some second, longer time period (e.g., three months). The "recovery index" contributor may be calculated based on the longest sleep period. Recovery index measures how long it takes for a user's resting heart rate to stabilize during the night. A sign of a very good recovery is that the user's resting heart rate stabilizes during the first half of the night, at least six hours before the user wakes up, leaving the body time to recover for the next day. The "body temperature" contributor may be calculated based on the longest sleep period (e.g., primary sleep period) or based on a nap happening after the longest sleep period if the user's highest temperature during the nap is at least 0.5° C. higher than the highest temperature during the longest period. In some aspects, the ring may measure a user's body temperature while the user is asleep, and the system 200 may display the user's average temperature relative to the user's baseline temperature. If a user's body temperature is outside of their normal range (e.g., clearly above or below 0.0), the body temperature contributor may be highlighted (e.g., go to a "Pay attention" state) or otherwise generate an alert for the user.

Figure 3:
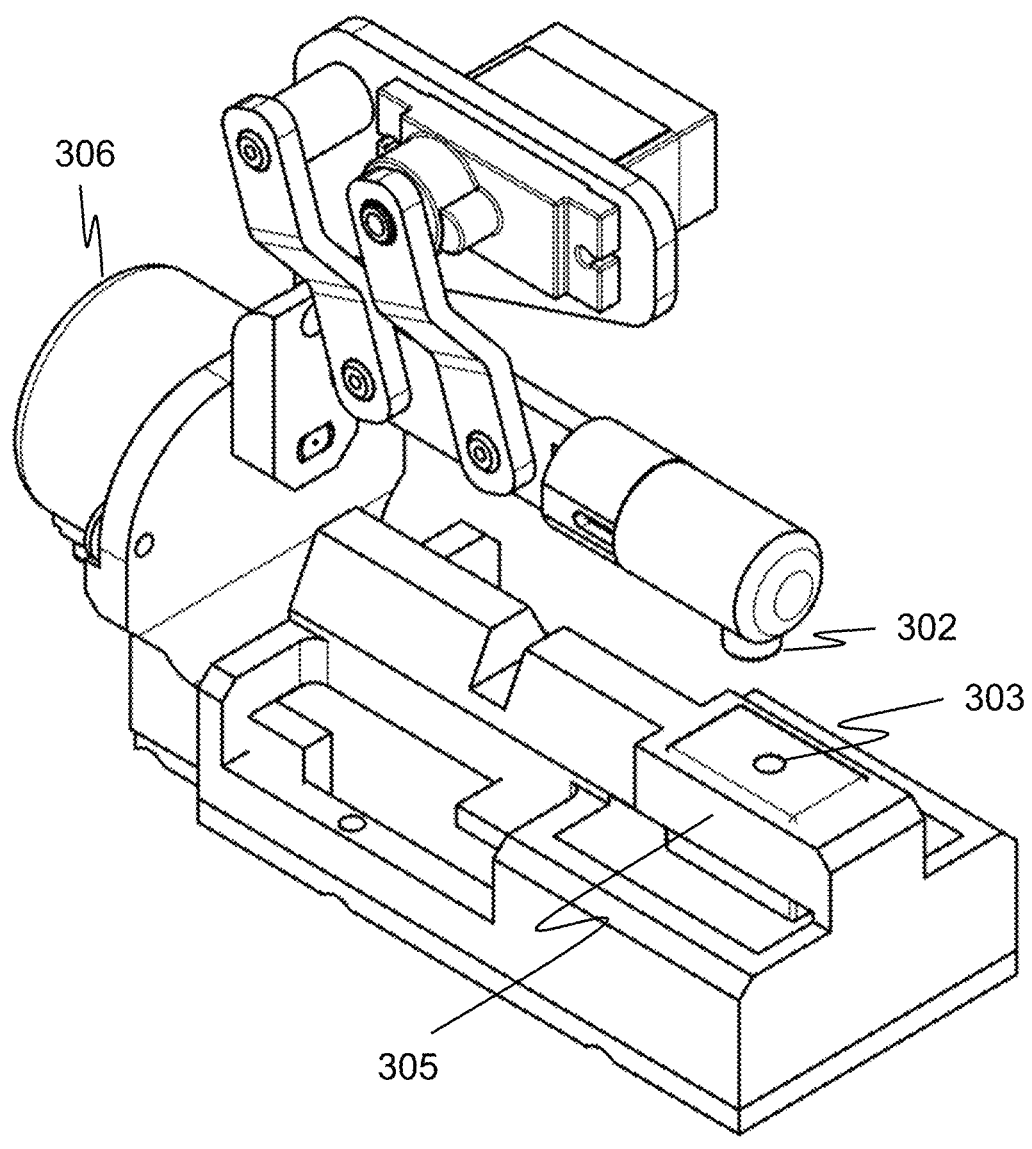
FIG. 3 is a schematic diagram of an example of a device in accordance with an embodiment of the present disclosure.

FIG. 3 is a schematic diagram of an example of a device 300 in accordance with an embodiment of the present disclosure.

The device 300 comprises a light source 302, a light detector 303, and a support 305 for receiving an appendage of a human body. The structure of the device 300 is well suited for receiving a finger, but it is clear that also other appendages of a human body, such as for example a wrist, an ankle, an arm, a leg, a toe, or an ear lobe, may be used.

The light source 302 may include light-emitting diodes (LEDs). The light source 302 may operate on a wide range of wavelengths. The light source 302 may emit white light. Additionally or alternatively, the wavelength range of the light source 302 may extend outside visible light wavelengths, e.g. from infrared wavelengths to ultraviolet wavelengths. In an embodiment, the light emitted at the light source 302 may originate from a source that is separate from the device 300 and the light may be guided to the light source 302 through an optical fiber.

The light detector 303 may be a spectrometer, which can distinguish intensities of different wavelengths including intensities of different colors. Additionally or alternatively, the light detector 302 may include photosensors, phototransistors, and photodiodes.

The device 300 is configured to move the light source 302. The movement may be caused for example by an actuator operatively connected to rear part 306 of the device 300. The actuator may be, for example, a motor or a manual pivot.

In operation, the light source 302 is configured to emit light and the light detector 303 is configured to detect light. A finger is placed on top of the support 305 and a measurement is started. An internal mechanism of the device 300 may be used for placing the light detector 303 against the finger. However, depending on the design, this is not mandatory as the support may be such that when the finger is placed on top of the support, the finger is by default against the light detector 303. Then the light source 302 is moved to at least two different measurement positions and the spectrum detected by the light detector 303 in the at least two different measurement positions is recorded.

The movement of the light source 302 may be a rotational movement around the support and thereby around the finger. Optionally, the device 300 may be configured to move the light source towards the finger and away from the finger at each measurement position so that the light source 302 may be arranged against the finger for the measurement and away from the finger for the rotational movement.

It is to be noted that FIG. 3 shows only one non-limiting example implementation of a device in accordance with various embodiments of the present disclosure and that various other implementations are possible within the scope of claims of present disclosure.

In an embodiment, there may be a calibration phase prior to the actual measurements by the device 300 of FIG. 3. Intensity and/or power of the light source 302 may be adjusted during such calibration phase in order to find adequate intensity that allows the signals to reach the light detector 303 during the measurements, while at the same time not increasing the intensity too high to saturate the light detector. The calibration phase may be performed prior to each measurement or every time the human appendage that is used in the measurement is changed, for example. In this way, distortion of measurement results due to variation in tissue thickness, skin tone, and other properties of the human appendage may be avoided or reduced.

FIGS. 4A-4F illustrate operation of example devices in accordance with various embodiments of the present disclosure. FIGS. 4A-4F show a finger 301, which is placed on a support of the device (support not shown in FIGS. 4A-4F).

Figure 4A:
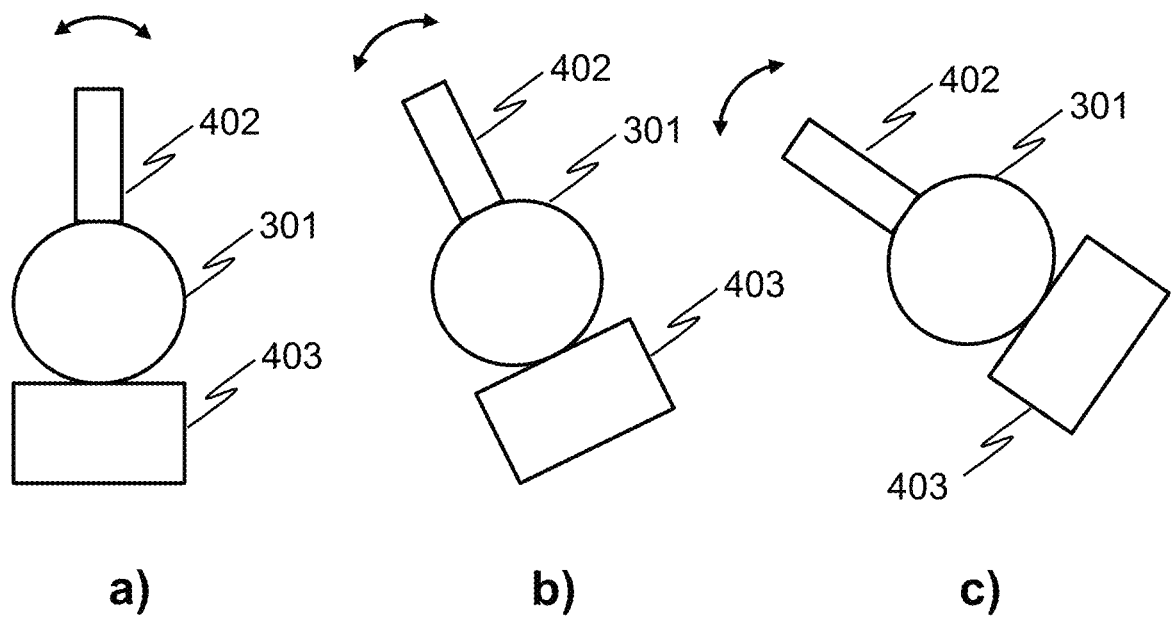
FIGS. 4A-4F illustrate operation of example devices in accordance with various embodiments of the present disclosure.

FIG. 4A shows an example in which one light source 402 and one light detector 403 move in synchronization in three different scenarios a, b, and c. That is, the position of the light source 402 and the light detector 403 in relation to each other stays the same while the light source 402 and the light detector 403 rotate around the finger 301. The finger 301 stays stationary. In scenario a) the light source 402 and the light detector 403 are on opposite sides of the finger 301 in a first measurement position. In scenario b) the light source 402 and the light detector 403 have been moved to reach a second measurement position. In the scenario c) the light source 402 and the light detector 403 have been moved to reach a third measurement position.

In some example embodiments, the light source 402 and the light detector 403 may be part of a wearable device such as ring 104 of FIGS. 1 and 2 and the movement of the light source 402 and the light detector 403 is effected by rotating the wearable device around the finger 301. The wearable device may be rotated by a user or by an external actuator that causes the rotation of the wearable device. Rotating the wearable device may be performed automatically by the external actuator. The external actuator may comprise one or more of the following: a motor, a manual pivot, or a friction wheel rotator. The user may perform rotating the wearable device in guidance of an application. The application may be communicatively connected to the wearable device for the purpose of collecting measurement data from the wearable device. The application may provide for example step-by-step instructions. An example of such instructions may guide the user as follows: rotate the wearable device 45 degrees, press a button, rotate the wearable device 45 degrees, press a button etc.

Figure 4B:
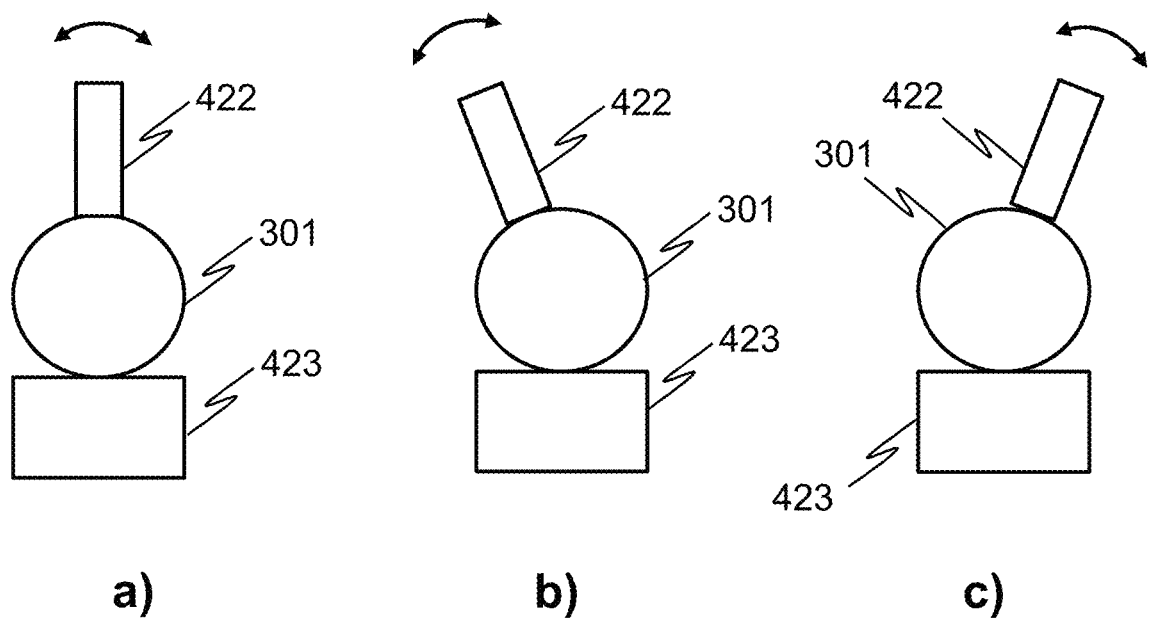

FIG. 4B shows an example in which the finger 301 and a light detector 423 stay stationary and one light source 422 moves in three different scenarios a, b, and c. In scenario a) the light source 422 and the light detector 423 are on opposite sides of the finger 301 in a first measurement position. In scenario b) the light source 422 has been moved to reach a second measurement position. In the scenario c) the light source 422 has been moved to reach a third measurement position.

Figure 4C:
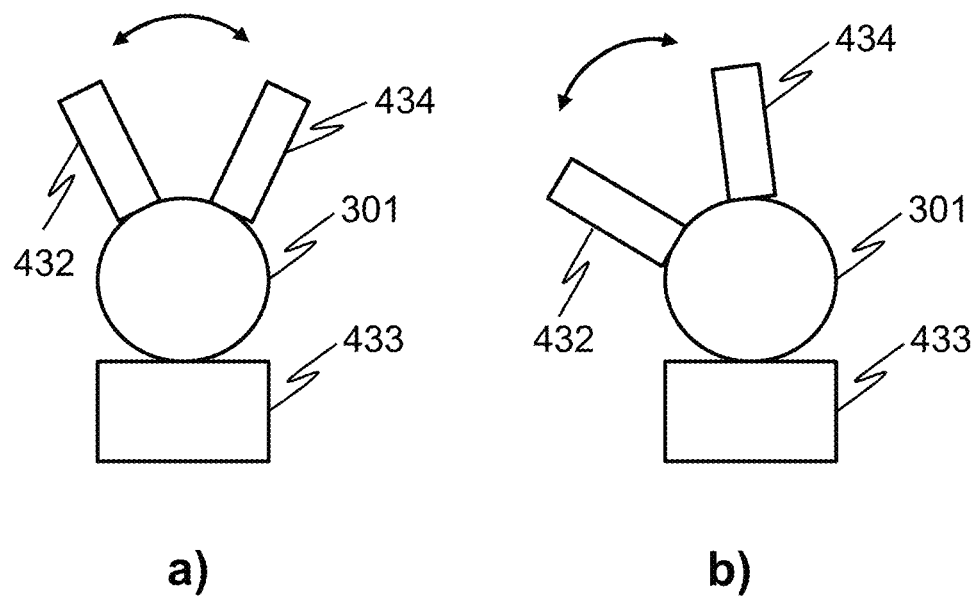

FIG. 4C shows an example in which the finger 301 and a light detector 433 stay stationary and two light sources 432 and 434 move in two different scenarios a and b. In this example, both light sources 432 and 434 are moved at the same time. In scenario a) the light sources 432 and 434 and the light detector 433 are in a first measurement position. In scenario b) the light sources 432 and 434 have been moved to reach a second measurement position.

Figure 4D:
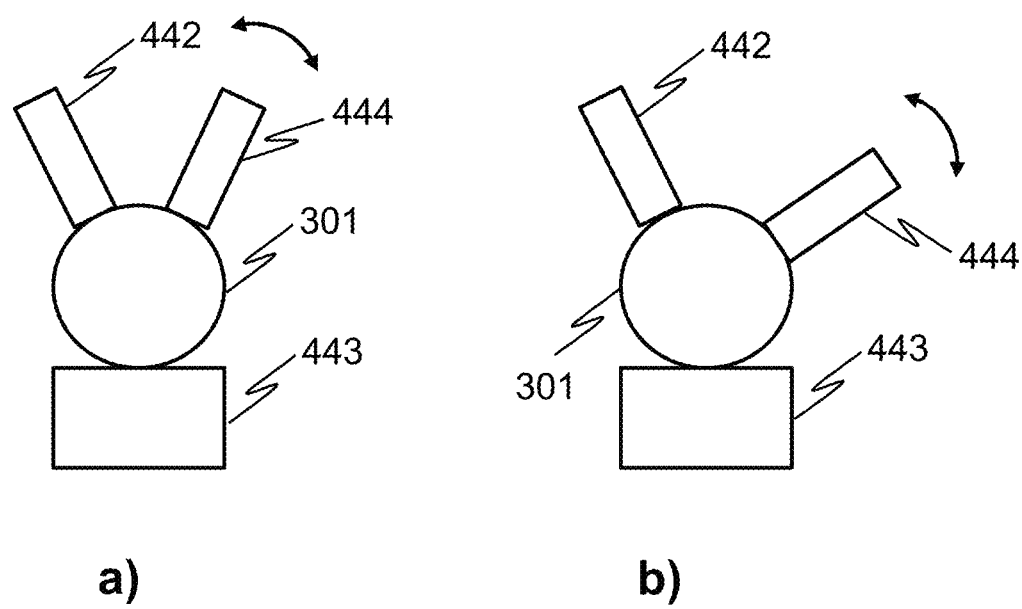

FIG. 4D shows an example in which the finger 301, a light detector 443 and a first light source 442 stay stationary and a second light source 444 moves in two different scenarios a and b. In scenario a) the light sources 442 and 444 and the light detector 443 are in a first measurement position. In scenario b) the light source 444 has been moved to reach a second measurement position.

Figure 4E:
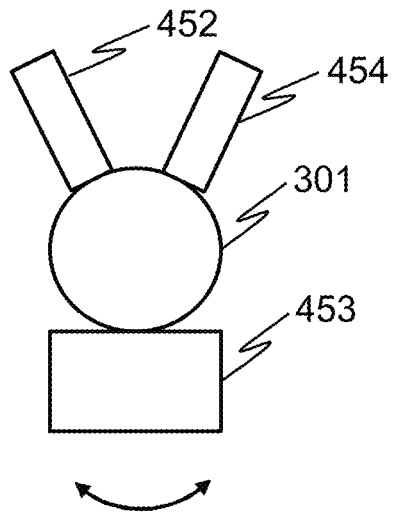
Figure 4E:
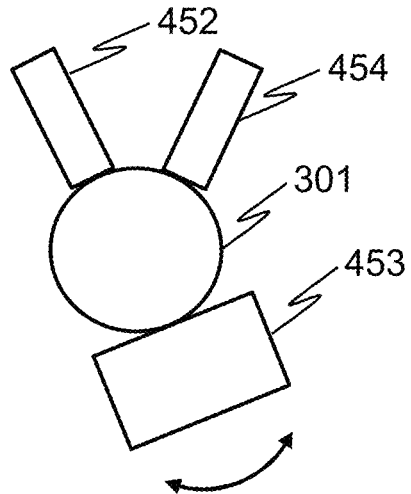

FIG. 4E shows an example in which the finger 301 and two light sources 452 and 454 stay stationary and a light detector 453 moves in two different scenarios a and b. In scenario a) the light sources 452 and 454 and the light detector 453 are in a first measurement position. In scenario b) the light detector 453 has been moved to reach a second measurement position.

Figure 4F:
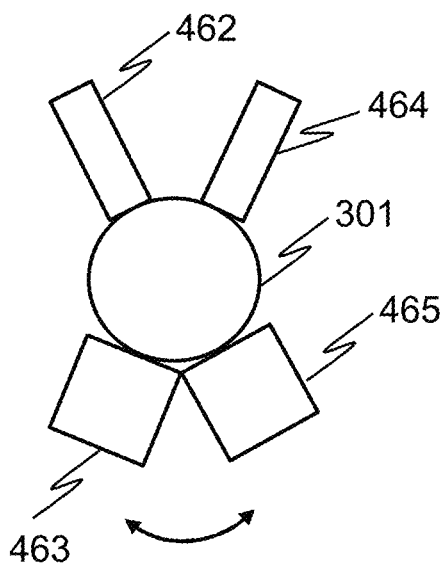
Figure 4F:
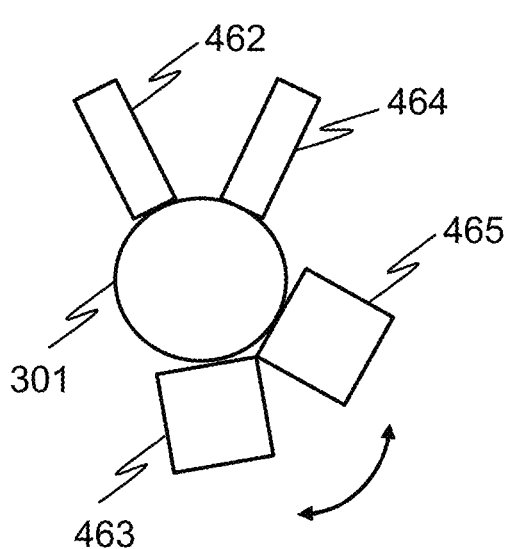

FIG. 4F shows an example in which the finger 301 and two light sources 462 and 464 stay stationary and two light detectors 463 and 465 move in two different scenarios a and b. In this example, both light detectors 463 and 465 are moved at the same time. In scenario a) the light sources 462 and 464 and the light detectors 463 and 465 are in a first measurement position. In scenario b) the light detectors 463 and 465 have been moved to reach a second measurement position.

FIGS. 4A-4F illustrate some non-limiting options for the movements of the light source(s) and/or light detector(s). It is clear that various further alternative options may be chosen for the movements of the light source(s), light detector(s), or both, within the scope of present disclosure.

Figure 5:
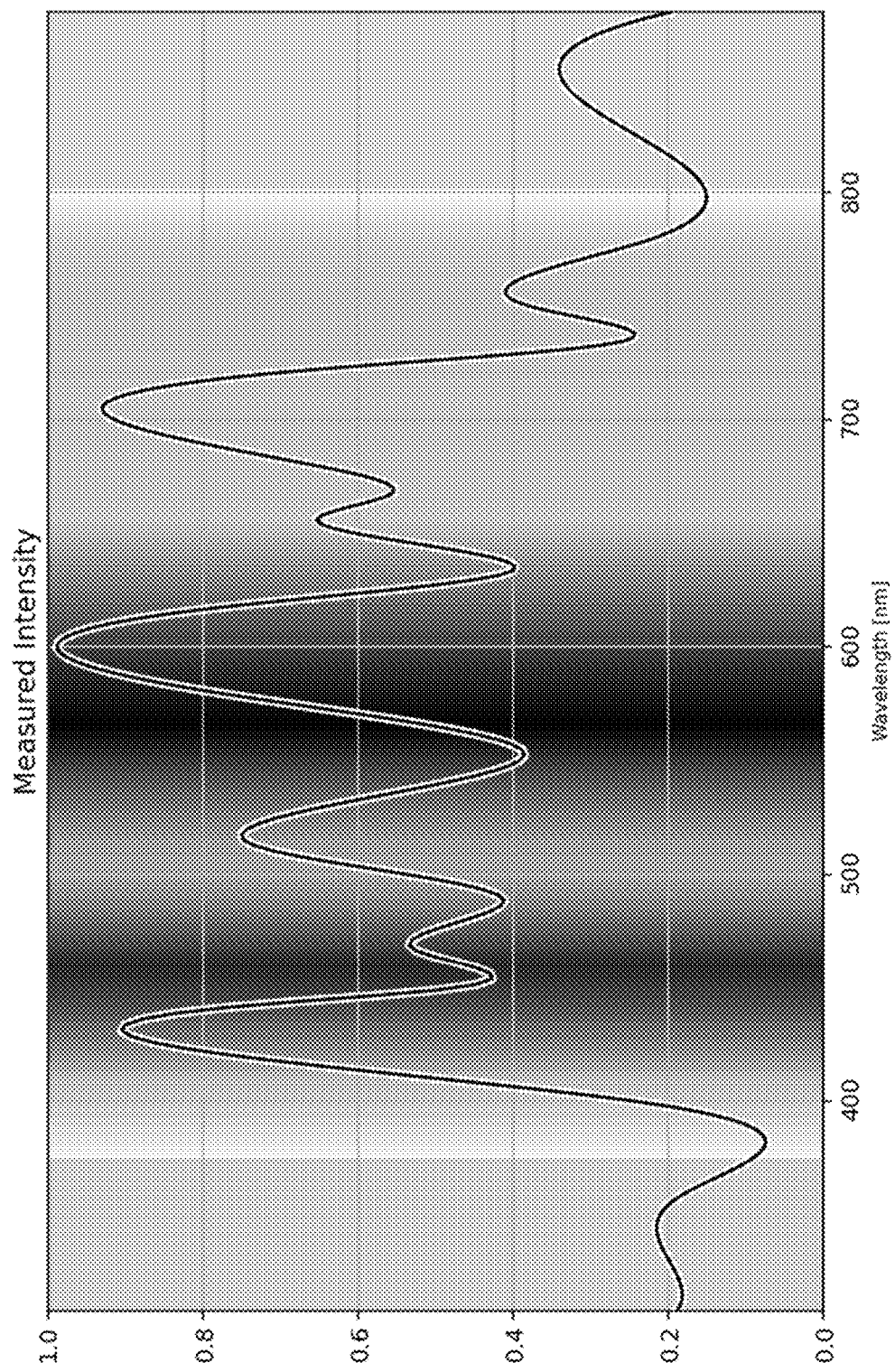
FIG. 5 shows a measurement result example obtained by an example device in accordance with an embodiment of the present disclosure.

FIG. 5 shows a measurement result example obtained by an example device in accordance with an embodiment of the present disclosure. FIG. 5 shows a graph of measured intensity at different wavelengths at one measurement position. Similar graphs may be obtained for a plurality of different measurement positions and for plurality of different human appendages (that is, e.g. fingers of different people) and thereby obtained plurality of measurement results may be used for studying and deciding on optimization of measurement locations of a wearable device sensor and/or optimization of wavelengths for the measurements in the wearable device sensor.

Figure 6:
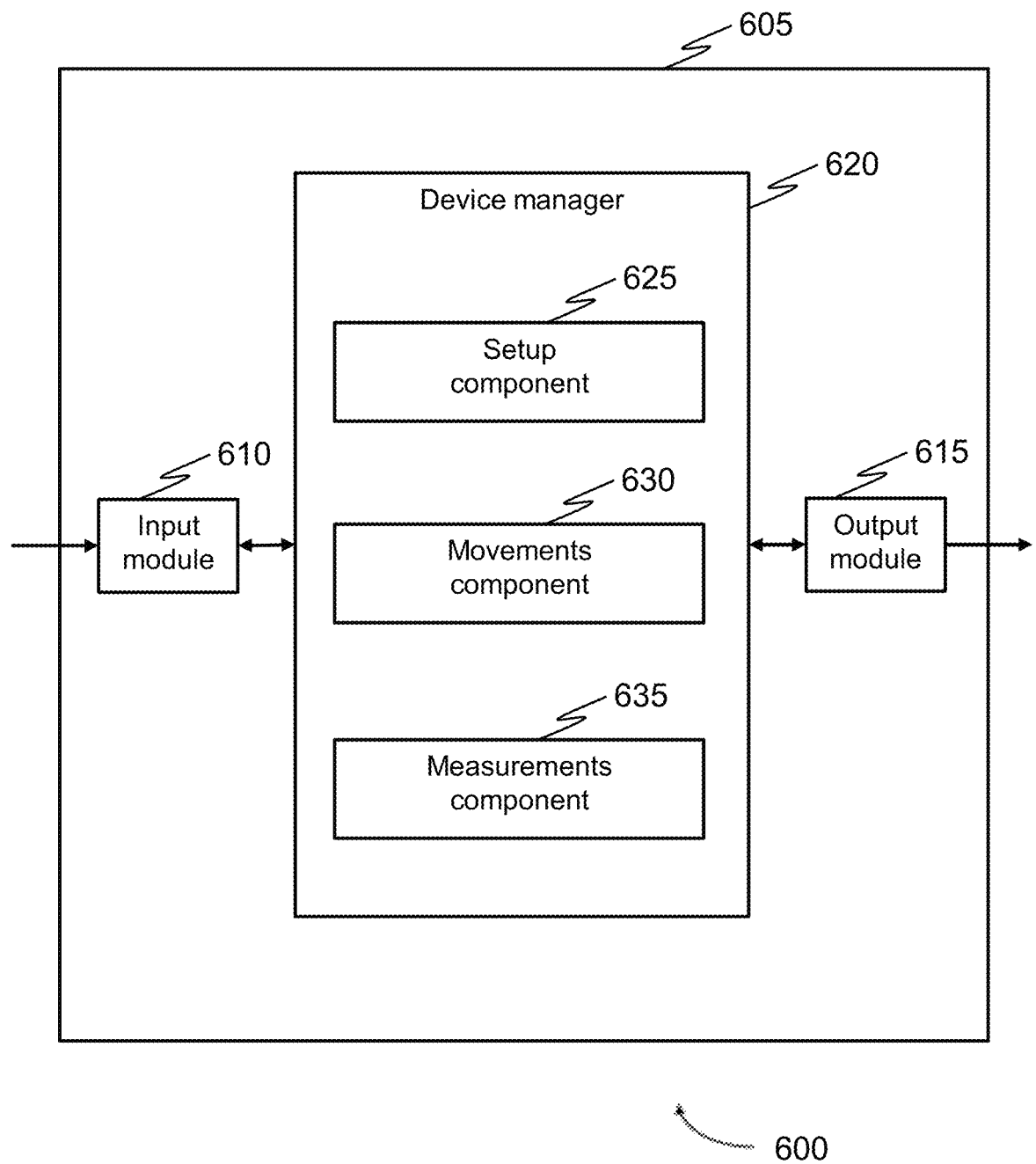
FIG. 6 shows a block diagram of an apparatus that supports measurements for a wearable device sensor in accordance with various embodiments of the present disclosure.

FIG. 6 shows a block diagram 600 of a device 605 that supports measurements for a wearable device sensor in accordance with various embodiments of the present disclosure. The device 605 may include an input module 610, an output module 615, and a device manager 620. The device 605 may also include a processor. Each of these components may be in communication with one another (e.g., via one or more buses).

The input module 610 may provide a means for receiving information such as packets, user data, control information, or any combination thereof. The information may be passed on to other components of the device 605. The input module 610 may be part of a user interface module.

The output module 615 may provide a means for transmitting signals generated by other components of the device 605. For example, the output module 615 may transmit information such as packets, user data, control information, or any combination thereof. In some examples, the output module 615 may be co-located with the input module 610 in a user interface module.

For example, the device manager 620 may include a setup component 625, a movements component 630, a measurements component 635, or any combination thereof. In some examples, the wearable device manager 620, or various components thereof, may be configured to perform various operations (e.g., receiving, monitoring, transmitting) using or otherwise in cooperation with the input module 610, the output module 615, or both. For example, the device manager 620 may receive information from the input module 610, send information to the output module 615, or be integrated in combination with the input module 610, the output module 615, or both to receive information, transmit information, or perform various other operations as described herein.

The device manager 620 may support measurements for a wearable device sensor in accordance with examples as disclosed herein. The setup component 625 may be configured as or otherwise support a means for receiving and/or detecting a human appendage on a support and for initiating a measurement for a wearable device sensor. The movements component 630 may be configured as or otherwise support a means for moving light source(s), light detector(s), or both, into two or more different measurement positions. The measurements component 635 may be configured as or otherwise support a means for collecting a plurality of measurement results from two or more measurement positions.

Figure 7:
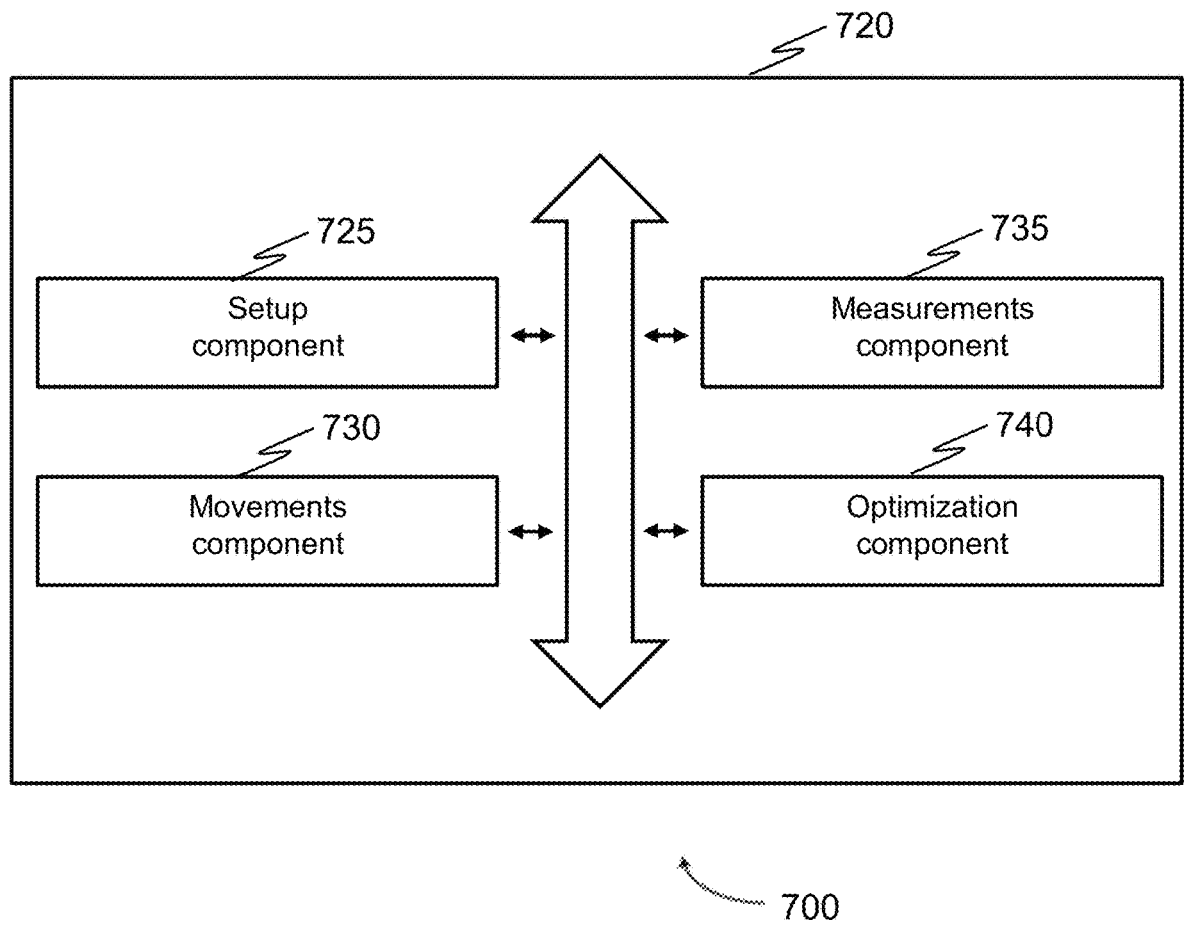
FIG. 7 shows a block diagram of a device manager that supports a device for measurements in accordance with various embodiments of the present disclosure.

FIG. 7 shows a block diagram 700 of a device manager 720 that supports measurements for a wearable device sensor in accordance with various embodiments of the present disclosure. The device manager 720 may be an example of aspects of a device manager or a device manager 620, or both, as described herein. The device manager 720, or various components thereof, may be an example of means for performing various aspects of measurements for a wearable device sensor as described herein. For example, the device manager 720 may include a setup component 725, a movements component 730, a measurements component 735, an optimization component 740, or any combination thereof. Each of these components may communicate, directly or indirectly, with one another (e.g., via one or more buses).

The device manager 720 may support measurements for a wearable device sensor in accordance with examples as disclosed herein. The setup component 725 may be configured as or otherwise support a means for receiving and/or detecting a human appendage on a support and for initiating a measurement for a wearable device sensor. The movements component 730 may be configured as or otherwise support a means for moving light source(s), light detector(s), or both, into two or more different measurement positions. The measurements component 735 may be configured as or otherwise support a means for collecting a plurality of measurement results from two or more measurement positions. The optimization component 740 may be configured as or otherwise support analyzing beneficial setup for a wearable device sensor at least in part based on the plurality of measurement results from the measurements component 735.

In some examples, the setup component 725 may be configured as or otherwise support a means for configuring a light source to emit light and a light detector to detect light to initiate a measurement for a wearable device sensor.

In some examples, the movements component 730 may be configured as or otherwise support a means for moving the light source(s), light detector(s), or both by a rotating movement around the support of the human appendage.

In some examples, the movements component 730 may be configured as or otherwise support a means for moving a light source and a light detector in synchronization.

In some examples, the movements component 730 may be configured as or otherwise support a means for moving a light source and a light detector independently from each other.

In some examples, the measurements component 735 may be configured as or otherwise support a means for measuring a rate of change of volume of the fluid through the artificial digit based at least in part on activating the wearable device sensor, wherein the plurality of measurements comprise the rate of change of volume.

In some examples, the optimization component 740 may be configured as or otherwise support a means for finding beneficial location(s) of light sources, beneficial locations of light detector(s) and/or beneficial wavelengths to be used in wearable device sensor.

Figure 8:
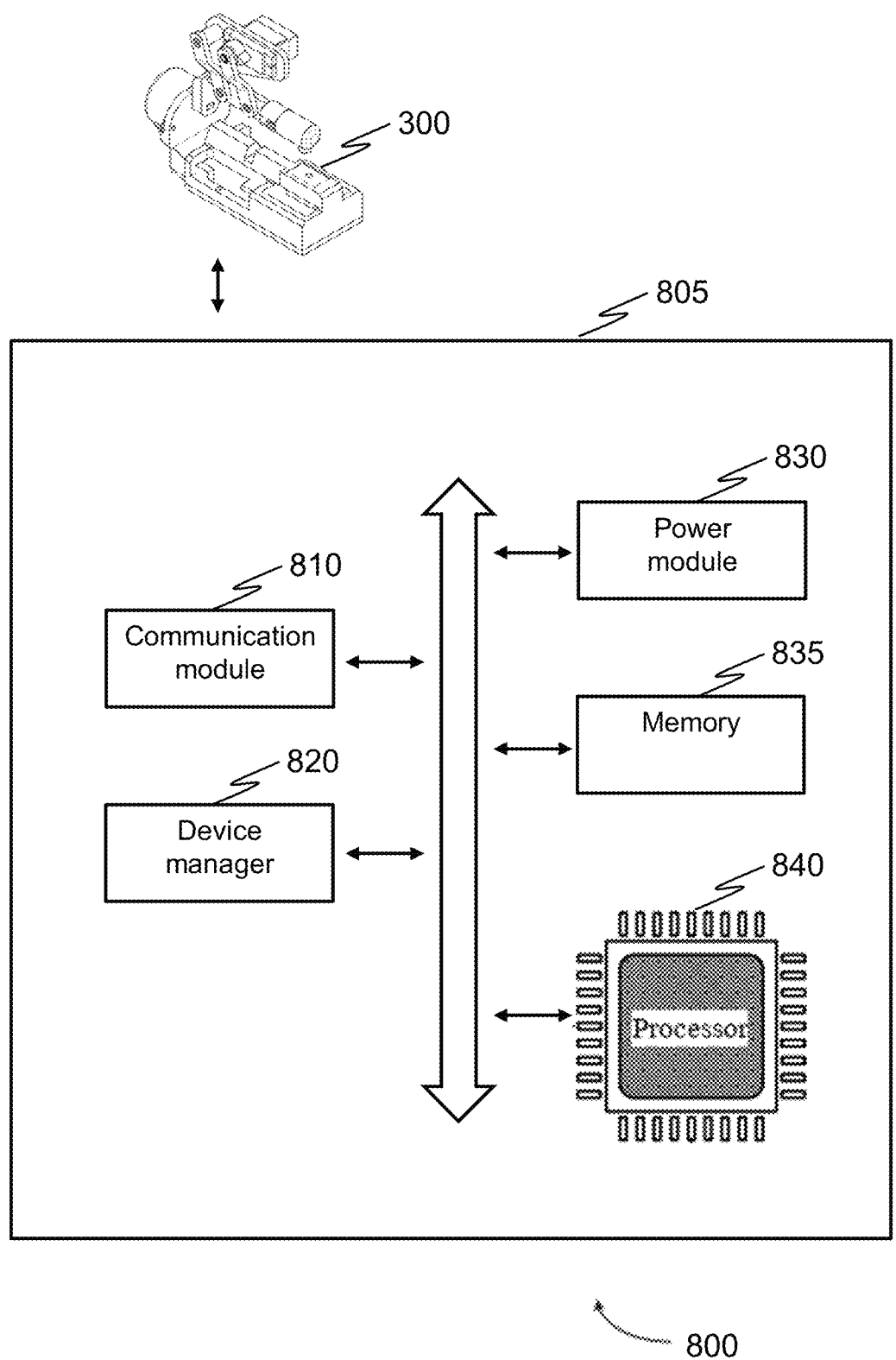
FIG. 8 shows a diagram of a system including a control device that supports measurements for a wearable device sensor in accordance with various embodiments of the present disclosure.

FIG. 8 shows a diagram of a system 800 including a control device 805 that supports a device 300 for measurement for a wearable device sensor in accordance with various embodiments of the present disclosure. The device 805 may be an example of or include the components of a device 605 as described herein. The device 805 may include components for bi-directional communications including components for transmitting and receiving communications with a device for measurement for a wearable device sensor, such as a device manager 820, a communication module 810, a power module 830, a memory 835, and a processor 840. These components may be in electronic communication or otherwise coupled (e.g., operatively, communicatively, functionally, electronically, electrically) via one or more buses (e.g., a bus 845).

FIG. 8 shows the control device 805 and the device for measurements 300 as separate devices, but in alternative implementations, the control device 805 may be integrated into the device for measurements 300.

The device manager 820 may support measurements for a wearable device sensor using the device 300 in accordance with examples as disclosed herein.

FIG. 9 shows a flow chart of a method of an example embodiment. The method supports measurements for a wearable device sensor in accordance with embodiments of the present disclosure. The operations of the method of FIG. 9 may be at least partially implemented for example by devices or components thereof described in FIGS. 3 through 8. In some examples, a control device may execute a set of instructions to control the functional elements of the control device to perform the described functions. Additionally, or alternatively, the control device may perform aspects of the described functions using special-purpose hardware.

At 910, the method may include arranging at least one light source and at least one light detector around an appendage of a human body and initiating a measurement for a wearable device sensor. The operations of 910 may be performed in accordance with examples as disclosed herein. In some examples, aspects of the operations of 910 may be performed by a setup component 625 as described with reference to FIG. 6.

At 920, the method may include moving the at least one light source, or the at least one light detector, or both to at least two different measurement positions in relation to the appendage of a human body. The operations of 920 may be performed in accordance with examples as disclosed herein. In some examples, aspects of the operations of 920 may be performed by a movements component 630 as described with reference to FIG. 6.

At 921, the method may include rotating the at least one light source, or the at least one light detector, or both around the appendage of the human body.

At 922, the method may alternatively include moving the at least one light source and the at least one light detector by rotating a wearable device comprising the light source and the light detector around the appendage of the human body. In some examples, the step 922 may include rotating the wearable device by a user. In some examples, the step 922 may include rotating the wearable device by a user in guidance of an application.

In some examples, the steps 920, 921 and 922 may include moving both the at least one light source and the at least one light detector in synchronization. In some examples, the steps 920 and 921 may include moving the at least one light source and the at least one light detector independently from each other. In some examples, the steps 920, 921 and 922 may be performed automatically.

At 930, the method may include collecting information relating to light detected by the at least one light detector from the at least two different measurement positions. The operations of 930 may be performed in accordance with examples as disclosed herein. In some examples, aspects of the operations of 930 may be performed by a measurements component 635 as described with reference to FIG. 6.

At 940, the method may include a further optional step of providing the collected information for optimizing one or more of the following in a wearable device sensor: location of one or more light sources, location of one or more light detectors, wavelengths used in the wearable device sensor. The operations of 940 may be performed in accordance with examples as disclosed herein. In some examples, aspects of the operations of 940 may be performed by an output module 615 as described with reference to FIG. 6.

In an embodiment, the method of FIG. 9 may further include a calibration phase prior to the actual measurements. Intensity and/or power of the light source may be adjusted during such calibration phase in order to find adequate intensity that allows the signals to reach the light detector, while at the same time not increasing the intensity too high to saturate the light detector. The calibration phase may be performed prior to each measurement or every time the human appendage that is used in the measurement is changed, for example. In this way, distortion of measurement results due to variation in tissue thickness, skin tone, and other properties of the human appendage may be avoided or reduced.

A device for test measurements for a wearable device sensor is described. The device may include a support configured to receive an appendage of a human body; at least one light source; at least one light detector; and an actuator configured to move the at least one light source, or the at least one light detector, or both to at least two different measurement positions in relation to the support.

In some examples of the devices described herein, the actuator is configured to rotate the at least one light source, or the at least one light detector, or both around the support.

In some examples of the devices described herein, the actuator is configured to automatically move the at least one light source, or the at least one light detector, or both.

In some examples of the devices described herein, the actuator is configured to move both the at least one light source and the at least one light detector in synchronization.

In some examples of the devices described herein, the actuator is configured to move the at least one light source and the at least one light detector independently from each other.

In some examples of the devices described herein, the actuator comprises a motor.

In some examples of the devices described herein, the actuator comprises a manual pivot.

In some examples of the devices described herein, the at least one light source and the at least one light detector are positioned substantially on opposite sides of the support.

In some examples of the devices described herein, the light detector is a spectrometer In some examples of the devices described herein, the light source has a wide wavelength range.

In some examples of the devices described herein, the wide wavelength range extends outside visible light wavelengths.

In some examples of the devices described herein, the wide wavelength range extends from infrared wavelengths to ultraviolet wavelengths.

In some examples of the devices described herein, the light source emits white light.

In some examples of the devices described herein, the device comprises two or more of said light sources.

In some examples of the devices described herein, the device comprises two or more of said light detectors.

In some examples of the devices described herein, the device comprises an output configured to output information relating to light detected by the at least one light detector at the at least two different measurement positions.

In some examples of the devices described herein, the appendage of a human body is a wrist, an ankle, an arm, a leg, a finger, a toe, or an ear lobe.

A method for performing measurement for a wearable device sensor is described. The method may include arranging at least one light source and at least one light detector around an appendage of a human body; moving the at least one light source, or the at least one light detector, or both to at least two different measurement positions in relation to the appendage of a human body, and collecting information relating to light detected by the at least one light detector from the at least two different measurement positions.

In some examples of the methods described herein, moving the at least one light source, or the at least one light detector, or both comprises rotating the at least one light source, or the at least one light detector, or both around the appendage of the human body.

In some examples of the methods described herein, moving the at least one light source, or the at least one light detector, or both comprises moving both the at least one light source and the at least one light detector in synchronization.

In some examples of the methods described herein, moving the at least one light source, or the at least one light detector, or both comprises moving the at least one light source and the at least one light detector independently from each other.

In some examples of the methods described herein, moving the at least one light source, or the at least one light detector, or both is performed automatically.

In some examples of the methods described herein, the at least one light source and the at least one light detector are comprised in a wearable device and moving the at least one light source and the at least one light detector is performed by rotating the wearable device around the appendage of a human body.

In some examples of the methods described herein, rotating the wearable device is performed automatically.

In some examples of the methods described herein, rotating the wearable device is performed by a user.

In some examples of the methods described herein, rotating the wearable device is performed by a user in guidance of an application.

In some examples of the methods described herein, the appendage of a human body is a wrist, an ankle, an arm, a leg, a finger, a toe, or an ear lobe.

In some examples of the methods described herein, the method further comprises providing the collected information for optimizing one or more of the following in a wearable device sensor: location of one or more light sources, location of one or more light detectors, wavelengths used in the wearable device sensor.

It should be noted that the methods described above describe possible implementations, and that the operations and the steps may be rearranged or otherwise modified and that other implementations are possible. Furthermore, aspects from two or more of the methods may be combined.

The description set forth herein, in connection with the appended drawings, describes example configurations and does not represent all the examples that may be implemented or that are within the scope of the claims. The term "exemplary" used herein means "serving as an example, instance, or illustration," and not "preferred" or "advantageous over other examples." The detailed description includes specific details for the purpose of providing an understanding of the described techniques. These techniques, however, may be practiced without these specific details. In some instances, well-known structures and devices are shown in block diagram form in order to avoid obscuring the concepts of the described examples.

In the appended figures, similar components or features may have the same reference label. Further, various components of the same type may be distinguished by following the reference label by a dash and a second label that distinguishes among the similar components. If just the first reference label is used in the specification, the description is applicable to any one of the similar components having the same first reference label irrespective of the second reference label.

Information and signals described herein may be represented using any of a variety of different technologies and techniques. For example, data, instructions, commands, information, signals, bits, symbols, and chips that may be referenced throughout the above description may be represented by voltages, currents, electromagnetic waves, magnetic fields or particles, optical fields or particles, or any combination thereof.

The various illustrative blocks and modules described in connection with the disclosure herein may be implemented or performed with a general-purpose processor, a DSP, an ASIC, an FPGA or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices (e.g., a combination of a DSP and a microprocessor, multiple microprocessors, one or more microprocessors in conjunction with a DSP core, or any other such configuration).

The functions described herein may be implemented in hardware, software executed by a processor, firmware, or any combination thereof. If implemented in software executed by a processor, the functions may be stored on or transmitted over as one or more instructions or code on a computer-readable medium. Other examples and implementations are within the scope of the disclosure and appended claims. For example, due to the nature of software, functions described above can be implemented using software executed by a processor, hardware, firmware, hardwiring, or combinations of any of these. Features implementing functions may also be physically located at various positions, including being distributed such that portions of functions are implemented at different physical locations. Also, as used herein, including in the claims, "or" as used in a list of items (for example, a list of items prefaced by a phrase such as "at least one of" or "one or more of") indicates an inclusive list such that, for example, a list of at least one of A, B, or C means A or B or C or AB or AC or BC or ABC (i.e., A and B and C). Also, as used herein, the phrase "based on" shall not be construed as a reference to a closed set of conditions. For example, an exemplary step that is described as "based on condition A" may be based on both a condition A and a condition B without departing from the scope of the present disclosure. In other words, as used herein, the phrase "based on" shall be construed in the same manner as the phrase "based at least in part on."

Computer-readable media includes both non-transitory computer storage media and communication media including any medium that facilitates transfer of a computer program from one place to another. A non-transitory storage medium may be any available medium that can be accessed by a general purpose or special purpose computer. By way of example, and not limitation, non-transitory computer-readable media can comprise RAM, ROM, electrically erasable programmable ROM (EEPROM), compact disk (CD) ROM or other optical disk storage, magnetic disk storage or other magnetic storage devices, or any other non-transitory medium that can be used to carry or store desired program code means in the form of instructions or data structures and that can be accessed by a general-purpose or special-purpose computer, or a general-purpose or special-purpose processor. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, include CD, laser disc, optical disc, digital versatile disc (DVD), floppy disk and Blu-ray disc where disks usually reproduce data magnetically, while discs reproduce data optically with lasers. Combinations of the above are also included within the scope of computer-readable media.

The description herein is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not limited to the examples and designs described herein, but is to be accorded the broadest scope consistent with the principles and novel features disclosed herein.

The invention claimed is:

1. A device for measurements for designing a wearable device sensor, the device comprising:
 a support configured to receive an appendage of a human body;
 at least one light source configured to move independently from the support;
 at least one light detector configured to move independently from the support, or to be integral to the support; and
 an actuator configured to move the at least one light source, or the at least one light detector, or both to at least two different measurement positions in relation to the support, wherein any two of the at least one light source, the at least one light detector, and the support are configured to be positioned substantially on opposite sides of the appendage.

2. The device according to claim 1, wherein the actuator is configured to rotate the at least one light source, or the at least one light detector, or both around the support.

3. The device according to claim 1, wherein the actuator is configured to automatically move the at least one light source, or the at least one light detector, or both.

4. The device according to claim 1, wherein the actuator is configured to synchronize movement between the at least one light source and the at least one light detector.

5. The device according to claim 1, wherein the actuator is configured to move the at least one light source and the at least one light detector independently from each other.

6. The device according to claim 1, wherein the actuator comprises a motor.

7. The device according to claim 1, wherein the actuator comprises a manual pivot.

8. The device according to claim 1, wherein the light detector is a spectrometer.

9. The device according to claim 1, wherein the light source has a wide wavelength range.

10. The device according to claim 9, wherein the wide wavelength range extends outside visible light wavelengths.

11. The device according to claim 9, wherein the wide wavelength range extends from infrared wavelengths to ultraviolet wavelengths.

12. The device according to claim 1, wherein the light source emits white light.

13. The device according to claim 1, wherein the device comprises two or more of said light sources.

14. The device according to claim 1, wherein the device comprises two or more of said light detectors.

15. The device according to claim 1, wherein the device comprises an output configured to output information relating to light detected by the at least one light detector at the at least two different measurement positions.

16. The device according to claim 1, wherein the appendage of a human body is a wrist, an ankle, an arm, a leg, a finger, a toe, or an ear lobe.

17. A method comprising:
performing measurement for designing a wearable device sensor by
arranging at least one light source and at least one light detector around an appendage of a human body, wherein the at least one light source and the at least one light detector are positioned substantially on opposite sides of the appendage;
moving the at least one light source, or the at least one light detector, or both to at least two different measurement positions in relation to the appendage of a human body, and
collecting information relating to light detected by the at least one light detector from the at least two different measurement positions.

18. The method according to claim 17, wherein moving the at least one light source, or the at least one light detector, or both comprises rotating the at least one light source, or the at least one light detector, or both around the appendage of the human body.

19. The method according to claim 17, wherein moving the at least one light source, or the at least one light detector, or both comprises moving-both synchronizing movement between the at least one light source and the at least one light detector-in-synchronization.

20. The method according to claim 17, wherein moving the at least one light source, or the at least one light detector, or both comprises moving the at least one light source and the at least one light detector independently from each other.

21. The method according to claim 17, wherein moving the at least one light source, or the at least one light detector, or both is performed automatically.

22. The method according to claim 17, wherein the at least one light source and the at least one light detector are comprised in a wearable device and moving the at least one light source and the at least one light detector is performed by rotating the wearable device around the appendage of the human body.

23. The method according to claim 17, wherein the appendage of a human body is a wrist, an ankle, an arm, a leg, a finger, a toe, or an ear lobe.

24. The method according to claim 17, wherein the method further comprises providing the collected information for optimizing one or more of the following in a wearable device sensor: location of one or more light sources, location of one or more light detectors, wavelengths used in the wearable device sensor.

* * * * *